US010828324B2

(12) United States Patent
Tsirikos-Karapanos

(10) Patent No.: US 10,828,324 B2
(45) Date of Patent: *Nov. 10, 2020

(54) PRODUCTION OF WATER-SOLUBLE HYDROLYZED CLINOPTILOLITE FRAGMENTS

(71) Applicant: Nikolaos Tsirikos-Karapanos, Cleveland, OH (US)

(72) Inventor: Nikolaos Tsirikos-Karapanos, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/278,669

(22) Filed: Feb. 18, 2019

(65) Prior Publication Data

US 2019/0175643 A1    Jun. 13, 2019

Related U.S. Application Data

(63) Continuation-in-part of application No. 15/461,332, filed on Mar. 16, 2017, now Pat. No. 10,206,948, which is a continuation-in-part of application No. 14/879,233, filed on Oct. 9, 2015, now Pat. No. 9,629,874, which is a continuation of application No. PCT/US2014/072923, filed on Dec. 31, 2014.

(60) Provisional application No. 62/061,898, filed on Oct. 9, 2014.

(51) Int. Cl.

| | |
|---|---|
| *A61K 33/06* | (2006.01) |
| *A61K 31/05* | (2006.01) |
| *A61K 31/198* | (2006.01) |
| *A61K 31/375* | (2006.01) |
| *A61K 31/385* | (2006.01) |
| *A61K 31/095* | (2006.01) |
| *A61K 31/352* | (2006.01) |
| *A61K 31/4745* | (2006.01) |
| *A23L 33/16* | (2016.01) |
| *A23L 33/15* | (2016.01) |
| *A61K 9/08* | (2006.01) |
| *A61K 9/00* | (2006.01) |
| *A61K 9/48* | (2006.01) |
| *A61K 9/14* | (2006.01) |
| *A61K 9/16* | (2006.01) |
| *A61K 9/20* | (2006.01) |

(52) U.S. Cl.
CPC .............. *A61K 33/06* (2013.01); *A23L 33/15* (2016.08); *A23L 33/16* (2016.08); *A61K 31/05* (2013.01); *A61K 31/095* (2013.01); *A61K 31/198* (2013.01); *A61K 31/352* (2013.01); *A61K 31/375* (2013.01); *A61K 31/385* (2013.01); *A61K 31/4745* (2013.01); *A23V 2002/00* (2013.01); *A23V 2200/30* (2013.01); *A23V 2250/026* (2013.01); *A23V 2250/15* (2013.01); *A23V 2250/21168* (2013.01); *A23V 2250/31* (2013.01); *A23V 2250/708* (2013.01); *A61K 9/0053* (2013.01); *A61K 9/0095* (2013.01); *A61K 9/08* (2013.01); *A61K 9/14* (2013.01); *A61K 9/16* (2013.01); *A61K 9/20* (2013.01); *A61K 9/48* (2013.01)

(58) Field of Classification Search
CPC ..... A23L 33/15; A23L 33/16; A23V 2002/00; A23V 2200/18; A23V 2200/30; A23V 2250/026; A23V 2250/15; A23V 2250/1564; A23V 2250/1628; A23V 2250/21168; A23V 2250/31; A23V 2250/708; A61K 31/05; A61K 31/095; A61K 31/198; A61K 31/352; A61K 31/375; A61K 31/385; A61K 31/4745; A61K 33/06; A61K 9/0053; A61K 9/0095; A61K 9/08; A61K 9/14; A61K 9/16; A61K 9/20; A61K 9/48
See application file for complete search history.

(56) References Cited

U.S. PATENT DOCUMENTS

| | | | |
|---|---|---|---|
| 6,288,045 B1 | 9/2001 | Kaufman | |
| 7,442,366 B2 | 10/2008 | Mueller et al. | |
| 9,629,874 B2 * | 4/2017 | Tsirikos-Karapanos | ..................... A23L 5/276 |
| 10,206,948 B2 * | 2/2019 | Tsirikos-Karapanos | ..................... A61K 33/06 |
| 2002/0034543 A1 | 3/2002 | Kirschner et al. | |

(Continued)

FOREIGN PATENT DOCUMENTS

| | | |
|---|---|---|
| DE | 2660682 C2 | 5/1988 |
| DE | 19681282 B4 | 10/2005 |

(Continued)

OTHER PUBLICATIONS

Jurkic et al (Nutrition and Metabolism, 2013, vol. 10, pp. 1-2) (Year: 2013).*

(Continued)

*Primary Examiner* — Mark V Stevens
(74) *Attorney, Agent, or Firm* — Jacob M. Ward; Ward Law Office LLC

(57) ABSTRACT

Methods are provided to make clinoptilolite into a water-soluble hydrolyzed form suitable for various administration routes, including oral administration. Absorption of water-soluble hydrolyzed clinoptilolite fragments can aid in detoxification by binding heavy metals and environmental toxins, can reduce reactive oxygen species and inflammation related to heavy metals and other/environmental toxins, resulting in an increase in energy, and/or in an increase in one or more of focus, concentration, and memory. Water-soluble hydrolyzed clinoptilolite fragments can be combined with one or more dietary supplements, including various vitamins and sleep aids.

18 Claims, 14 Drawing Sheets

(56) References Cited

U.S. PATENT DOCUMENTS

| | | | |
|---|---|---|---|
| 2003/0105031 A1* | 6/2003 | Rosenbloom | A61K 8/42 514/27 |
| 2005/0031708 A1 | 2/2005 | Portney | |
| 2011/0064798 A1* | 3/2011 | Suvee | C05G 5/27 424/451 |
| 2011/0081405 A1 | 4/2011 | Mikloska et al. | |
| 2017/0107121 A1* | 4/2017 | Cook | C02F 1/281 |

FOREIGN PATENT DOCUMENTS

| | | |
|---|---|---|
| DE | 202010013541 U1 | 1/2011 |
| GB | 2510659 A | 8/2014 |
| WO | 00/75079 A1 | 12/2000 |
| WO | 2008092275 A1 | 8/2008 |
| WO | 2010018418 A1 | 2/2010 |

OTHER PUBLICATIONS

Akkoca et al., "Hydrothermal and thermal treatment of natural clinoptilolite zeolite from Bigadi double dagger, Turkey: An experimental study", Geochemistry International, Jun. 2013, vol. 54(6) pp. 495-504.

De las Pozas et al, "Modification of clinoptilolite by leaching with orthophosphoric acid", Microporous Materials, Jan. 1996, vol. 5(5).

Kaufman, Harvey, "Modern Detox for Today's Toxic World (ZNatural)", Dec. 31, 2013.

Hernandez-Beltran et al., (Journal of Inclusion Phenom Macrocycl Chem) "Effect of acid phosphate media on the stability of clinoptilolite-rich tuff", Jun. 30, 2008, vol. 61, pp. 93-100.

Karel et al., "Development of Silver Ion Doped Antibacterial Clays and Investigation of Their Antibacterial Activity", Dec. 31, 2015.

Panneerselvam et al., "Phosphoric acid modified-Y zeolites: A novel, efficient and versatile ion exchanger", Nov. 11, 2008.

Murphy et al., "Reaction kinetics and thermodynamics of aqueous dissolution and growth of analcime and Na-clinoptilolite at 25 degrees C", Feb. 29, 1996.

Liberti et al., "Phosphates and Ammonia Recovery From Secondary Effluents by Selective Ion-Exchange With Production of a Slow-Release Fertilizer", Jan. 31, 1979.

Xu et al., "Dealumination of clinoptilolite and its effect on zinc removal from acid rock drainage", Sep. 30, 2014.

SaltsClaysMinerals.com (http://www.saltsclaysminerals.com/natural/ZC-20.html, Natural Zeolite Clinoptilolite <40 Micron, 2016).

Pansini (Mineral Deposita, 1996, vol. 31, pp. 563-575).

Anonymous. Cellular Detoxing. May 18, 2014. Retrieved from Internet Archive, Wayback Machine website. original URL: http://detoxingdrops.com.

Jurkic et al. "Biological and Therapeutic Effects of Ortho-Silicic Acid and Some Ortho-Silicic Acid-Releasing Compounds." Nutrition & Metabolism 2013, 10:2 http://www.nutritionandmetabolism.comicontent/10/1/2; Department of Biotechnology, University of Rijeka, Croatia; BioMed Central Ltd. Jan. 8, 2013 pp. 1-12.

Hernandez-Beltran et al., "Elemental Composition Variability of clinoptilolite-rich tuff after the Treatment with Acid Phosphate Solutions", Sep. 19, 2007, www.sciencedirect.com; Hydrometallurgy 89 (2007) 374-378.

Jugdaohsingh et al. "Oligomeric but not Monomeric Silica Prevents Aluminum Absorption in Humans" 2000 American Society for Clinical Nutrition—vol. 71 pp. 944-949.

Thomas E. Cook et al: "Zeolite A hydrolysis and degradation", Environmental Science & Technology, vol. 16, No. 6, Jun. 1982, pp. 344-350, XP055447114, ISSN: 0013-936X, DOI: 10.1021/ES00100a008.

* cited by examiner

PRODUCTION OF WATER-SOLUBLE HYDROLYZED CLINOPTILOLITE FRAGMENTS

CROSS-REFERENCE TO RELATED APPLICATIONS

This application is a continuation-in-part of U.S. patent application Ser. No. 15/461,332, filed on Mar. 16, 2017, which in turn is a continuation-in-part of U.S. patent application Ser. No. 14/879,233, filed on Oct. 9, 2015, which issued as U.S. Pat. No. 9,629,874 on Apr. 25, 2017, which in turn claims the benefit of International Application No. PCT/US2014/072923, filed on Dec. 31, 2014, and U.S. Provisional Application No. 62/061,898, filed on Oct. 9, 2014. The entire disclosures of the above applications are hereby incorporated herein by reference.

FIELD

The present technology relates to ways of making and using water-soluble and bio-absorbable clinoptilolite fragments and compositions thereof.

BACKGROUND

This section provides background information related to the present disclosure which is not necessarily prior art.

The zeolite clinoptilolite, a microporous arrangement of silica and alumina tetrahedra (e.g., sodium aluminosilicate) is a non-water-soluble, non-bioabsorbable salt with a three-dimensional honeycomb configuration. Due to its three-dimensional configuration, clinoptilolite can attract and retain various heavy metals in vitro. Based on this property, clinoptilolite is used in commercially available filters in various applications ranging from household water filtration to oil industry gas filtration. Several attempts have been made to take advantage of the properties of clinoptilolite in vivo. Such attempts, including associated commercially available nutrition supplement products, have included simple water suspensions of clinoptilolite and not water-soluble solutions thereof. These products fail to bring clinoptilolite's ability to remove heavy metals in vivo. If orally administered, a clinoptilolite water suspension will release clinoptilolite into the gastrointestinal (GI) tract, but this will not result in GI absorption of clinoptilolite. Clinoptilolite administered in this fashion is simply eliminated from the body after a number of bowel movements.

There is a need for a water-soluble clinoptilolite formulation that can be orally administered and absorbed in the GI tract, where the absorbed clinoptilolite retains the ability to bind various heavy metals.

SUMMARY

In concordance with the instant disclosure, a water-soluble clinoptilolite formulation that can be orally administered and absorbed in the GI tract, where the absorbed clinoptilolite retains the ability to bind various heavy metals, is surprisingly discovered.

The present technology includes compositions and methods that relate to formation and use of a water-soluble and bio-absorbable hydrolyzed clinoptilolite derived product, which can be used as a supplement within the scope of systemic, cellular detoxification. Water-soluble hydrolyzed clinoptilolite fragments can be absorbed in the GI tract and can be used alone or in combination with various components as a dietary supplement. The PAPMA test results, detailed further herein, show that product of the present disclosure can cross cellular membranes. Thus, the fragments can circulate further than the GI tract and have the capability to offer systemic detoxification. In this context, "systemic" means that the product acts in more than one human body compartments. Compositions include water-soluble hydrolyzed clinoptilolite fragments and a dietary supplement, such as a vitamin, mineral, fiber, fatty acid, amino acid, herb, herbal extract, and combinations thereof. In certain embodiments, water-soluble hydrolyzed clinoptilolite fragments are combined with vitamin C. In some embodiments, water-soluble hydrolyzed clinoptilolite fragments are combined with a sleep aid, such as L-tryptophan, optionally L-theanine, chamomile, lemon balm, passion flower, hops, valerian, and combinations thereof.

Methods of making water-soluble hydrolyzed clinoptilolite fragments are provided. Such methods include performing a hydrolysis reaction by hydrolyzing clinoptilolite with an acid and separating the hydrolysis reaction into a liquid portion and a solid portion, the liquid portion including a hydrolysis reaction product including water-soluble hydrolyzed clinoptilolite fragments. Phosphoric acid can be used in the hydrolysis reaction. The hydrolysis reaction can also involve heating and agitating the clinoptilolite and acid.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
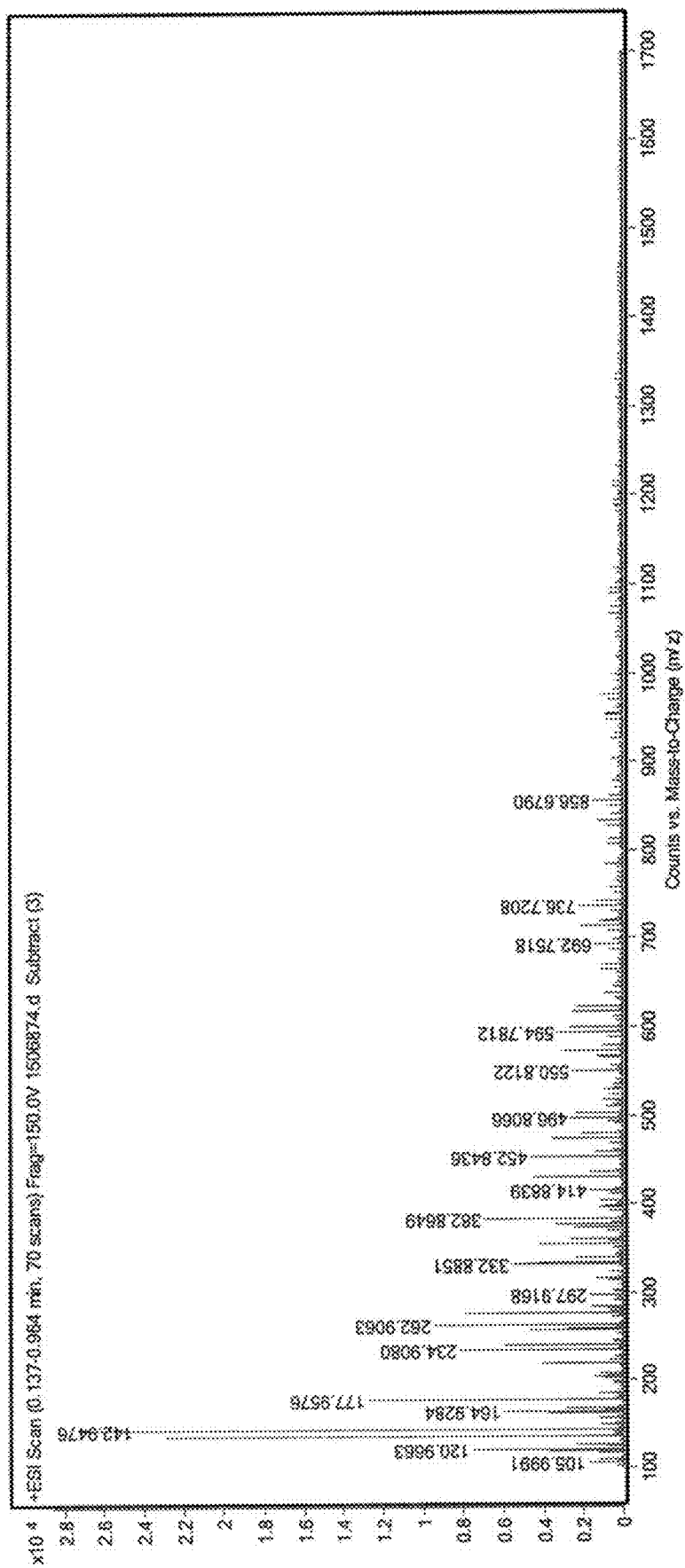
FIG. 1 depicts a spectrogram obtained from liquid chromatography-mass spectrometry (LC-MS) analysis of water-soluble hydrolyzed clinoptilolite fragments having a range of molecular weights between 100-1000 Daltons produced according to the present technology.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology includes water-soluble hydrolyzed clinoptilolite fragments, compositions including water-soluble hydrolyzed clinoptilolite fragments, and methods of making water-soluble hydrolyzed clinoptilolite fragments. Clinoptilolite can include a natural zeolite with a microporous arrangement of silica and alumina tetrahedra. Clinoptilolite has the IUPAC name aluminum sodium dioxido (oxo) silane, and can be referred to as sodium aluminosilicate or aluminum sodium silicate. Its structure can include an outer framework of silica and alumina tetrahedra, within which water molecules and exchangeable cations (e.g., calcium, potassium, sodium) can migrate. The molecular formula of clinoptilolite can vary in composition, where representative examples can be embodied by the following molecular formulas: $(K_{0-1}Na_{0-1}Ca_{0-0.5})_6(Al_6Si_{30}O_{72}) \cdot 2H_2O$; $(Na,K,Ca)_{2-3}Al_3(Al,Si)_2Si_{13}O_{36} \cdot 12H_2O$; $(Na_2,K_2,Ca)_3Al_6Si_{30}O_{72} \cdot 24H_2O$, and $(Na,K)_6(Al_6Si_{30}O_{72}) \cdot 20H_2O$. As provided herein, water-soluble hydrolyzed clinoptilolite fragments include aqueous solutions of water-soluble and bio-absorbable mixtures of zeolite clinoptilolite fragments. Water-soluble hydrolyzed clinoptilolite fragments can be produced by hydrolyzing natural zeolite clinoptilolite under heating with the use of an acid, such as phosphoric acid.

A natural zeolite including clinoptilolite can be hydrolyzed to form water-soluble hydrolyzed clinoptilolite fragments. The natural zeolite can be made water-soluble and provide a certain profile of hydrolyzed fragments using the processes disclosed herein. Examples of natural zeolites include zeolites from St. Cloud Mining Company (Winston, N. Mex.), including clinoptilolite obtained from Winston, N. Mex. that includes calcium aluminosilicate and clinoptilolite obtained from Ash Meadows, Nev. that includes sodium aluminosilicate.

In certain embodiments, the natural zeolite that is hydrolyzed to form water-soluble hydrolyzed clinoptilolite fragments is NV—Na*Ash Meadows Clinoptilolite that includes hydrous sodium aluminosilicate from St. Cloud Mining Company (Winston, N. Mex.). Table 1 shows typical properties for this zeolite.

TABLE 1

| | |
|---|---|
| Form | Granules & Powders |
| Color | Tan - Green |
| Pore Diameter | 4.0 Angstroms |
| Pore Volume | 15% |
| Specific Surface Area | 40 m$^2$/g |
| Bulk | 45-80 lbs/ft$^3$ |
| | 760-1,283 kg/m$^3$ |
| Solid Density | 100 lbs/ft$^3$ |
| | 1,603 kg/m$^3$ |
| Alkali Stability | pH of 7-10 |
| Acid Stability | pH of 3-7 |
| Thermal Stability | 1,202° F. 650° C. |

A typical chemical analysis for the zeolite can include the component percentages shown in Table 2.

TABLE 2

| SiO$_2$ | Al$_2$O$_3$ | Fe$_2$O$_3$ | CaO | MgO | Na$_2$O | K$_2$O | MnO | TiO$_2$ |
|---|---|---|---|---|---|---|---|---|
| 69.1 | 11.9 | 0.7 | 0.8 | 0.4 | 3.5 | 3.8 | 0.02 | 0.1 |

The zeolite can exhibit ion exchange with the cations; as nonlimiting examples are the cations: $Rb^+$, $Na^+$, $Ba^{+2}$, $Mg^{+2}$, $Li^+$, $Ag^+$, $Sr^{+2}$, $Fe^{+3}$, $K^+$, $Cd^{+2}$, $Cu^{+2}$, $Co^{+3}$, $Cs^+$, $Pb^{+2}$, $Ca^{+2}$, $Al^{+3}$, $NH_4^+$, $Zn^{+2}$, $Hg^{+2}$, and $Cr^{+3}$. It should be understood that other cations may also be used within the scope of the present disclosure.

Water-soluble hydrolyzed clinoptilolite fragments can be produced as follows. A hydrolysis reaction can be used to produce the water-soluble hydrolyzed clinoptilolite fragments, where the hydrolysis reaction progress can be monitored over time; e.g., the hydrolysis reaction can proceed over several hours to several days. In certain embodiments, the hydrolysis reaction can be performed over the course of a day. The hydrolysis product (i.e., water-soluble hydrolyzed clinoptilolite fragments) can be recovered, for example, by siphoning and filtering the product.

The hydrolysis reaction can include the following aspects. A reaction mixture can be prepared including clinoptilolite, an acid (e.g., phosphoric acid), and water. The reaction mixture can be assembled by heating the water and adding the clinoptilolite while agitating the reaction mixture in some fashion, for example, by stirring the heated water while dispensing the clinoptilolite at a rate that minimizes clumping in order to form a relatively uniform slurry. The phosphoric acid can be added to the clinoptilolite-water mixture. Addition of the phosphoric acid can be at a rate that maintains a desired temperature profile for the reaction mixture, where agitation or stirring can maintain the reaction mixture as a slurry during the phosphoric acid addition. Heating can be continued as necessary for completion of the hydrolysis reaction. Once completed, the reaction mixture can be allowed to cool.

Completion of the hydrolysis reaction can be monitored as follows. At various time intervals, such as every hour, half-hour, or quarter-hour, stirring and heating of the reaction mixture can be stopped. Morphology of the mixture surface can be observed. Heating and stirring of the reaction mixture can be continued if the hydrolysis reaction is not yet complete. The hydrolysis reaction and monitoring thereof can be continued.

Siphoning and filtration of the hydrolysis reaction product can include the following aspects. The hydrolysis reaction product can be cooled to room temperature and the reaction mixture can be allowed to settle. Settling can result in two layers or portions, including a substantially liquid layer or portion and a substantially solid layer or portion, where the liquid layer includes the hydrolysis reaction product. The liquid layer can be separated from the solid layer by siphoning and/or decanting. The liquid layer can be further filtered to obtain a substantially transparent liquid that can have a light yellowish tint. The liquid layer can be stored thereafter, where storage can include refrigeration of the liquid layer.

The liquid layer including the hydrolysis reaction product can be characterized as follows. The liquid layer can have an acidic pH, for example, a pH that can range from 4.0 to 5.5, including a range of 4.7 to 4.9. The liquid layer can have a solid portion, for example, a solid portion of about 15-21 mg/ml, including about 17-19 mg/ml. Determination of solids can be performed by taking a certain volume of the liquid layer including the hydrolysis reaction product (e.g., 30-50 ml) and allowing the liquid portion to evaporate. For example, the liquid layer volume can be placed on an evaporating plate and left in a warm chamber at 60° C. for 24 hours. The solid portion can be weighed once the liquid is evaporated.

It should be appreciated that the liquid layer of the present disclosure includes an aqueous solution containing dissolved water-soluble hydrolyzed clinoptilolite fragments, which is different from a suspension of clinoptilolite in water and/or a suspension of clinoptilolite fragments in water. In certain embodiments, the water-soluble hydrolyzed clinoptilolite fragments are present in a concentration from about 5 mg/ml to about 50 mg/ml. In other embodiments, the water-soluble hydrolyzed clinoptilolite fragments are present in a concentration from about 10 mg/ml to about 36 mg/ml. In a most preferred embodiment, the water-soluble hydrolyzed clinoptilolite fragments are present in a concentration from about 15 mg/ml to about 21 mg/ml. One of ordinary skill in the art may select other suitable concentrations for the water-soluble hydrolyzed clinoptilolite fragments in the aqueous solution, as desired.

Water-soluble hydrolyzed clinoptilolite fragments in the hydrolysis product can be characterized as follows. Liquid chromatography with mass spectrometry (LC-MS) can be performed to determine the transformation of non-water-soluble zeolite clinoptilolite to water-soluble hydrolyzed clinoptilolite fragments. Suitable equipment for performing LC-MS include an Agilent 1200 HPLC, Agilent 6210 TOF Mass Spectrometer with Electrospray Ionization. The hydrolysis product including the water-soluble hydrolyzed clinoptilolite fragments can be diluted into a mobile phase for analysis by direct injection mass spectrometry. The mobile phase can include 50/50 acetonitrile/water with 0.1% formic acid. The sample can be injected into the mobile phase stream, which can be electrosprayed into the TOF mass spectrometer. LC-MS can confirm that the result of the zeolite clinoptilolite hydrolysis as described herein is an aqueous solution of hydrolyzed zeolite clinoptilolite derived fragments.

FIGS. 1-6 each provide an example of a mass spectrum obtained for six different preparations of water-soluble hydrolyzed clinoptilolite fragments. As can be seen, mass spectrometric analysis of the water-soluble hydrolyzed clinoptilolite fragments can yield a range of molecular weights ranging from 100 to 1,000 Daltons, including a range of 218 to 620 Daltons. The exact mass for each of the observed peaks and the difference between adjacent peaks can be used to determine the presence of sodium ions. At least one sodium ion can be associated with each of the various molecular weight species of water-soluble hydrolyzed clinoptilolite fragments. Repeating units of 98 Daltons and 120 Daltons can be observed. The water-soluble hydrolyzed clinoptilolite fragments have substantially lower molecular weights than the starting zeolite material, where these lower molecular weights can contribute to the water-soluble nature of the hydrolyzed clinoptilolite fragments and can contribute to improved absorption and uptake of the water-soluble hydrolyzed clinoptilolite fragments in the body.

Water-soluble hydrolyzed clinoptilolite fragments can be provided alone and in various compositions and formulations, including various supplement combinations and nutraceutical products. As described herein, the precursor material used to produce the water-soluble hydrolyzed clinoptilolite fragments is the natural zeolite clinoptilolite. Nutraceutical products including food additives can be subject to premarket review and approval by the U.S. Food & Drug Administration (FDA), where under FDA 21 CFR they can be granted GRAS (Generally Regarded As Safe) status. The zeolite clinoptilolite (sodium aluminosilicate) has an FDA GRAS Status as of April 2014 (FDA 21 CFR § 182.2727 and food additive E-number: E-554). The starting zeolite material, along with several of the additional components described herein, can be found on the Toxic Substances Control Act List as GRAS materials.

Water-soluble hydrolyzed clinoptilolite fragments can be diluted to desired amounts or percentages by weight. For example, the hydrolysis product obtained using the methods described herein can have a solid portion of about 15-21 mg/mL, corresponding to 1.5-2.1% by weight water-soluble hydrolyzed clinoptilolite fragments. Dilution can be with sterile, distilled, and deionized water. Solutions of the water-soluble hydrolyzed clinoptilolite fragments and water used to dilute the water-soluble hydrolyzed clinoptilolite fragments can also include various stabilizers and/or preservatives. For example, sodium benzoate and/or potassium sorbate can be used. The water-soluble hydrolyzed clinoptilolite fragments can be diluted with water and optional stabilizers and/or preservative(s) to produce solutions have certain pH values and solid portions. For example, diluted water-soluble hydrolyzed clinoptilolite fragment solutions can have a pH of 4.0±1.5 and a solid portion of 0.35-9.00 mg/ml (i.e. 0.35%-0.9% by weight).

The special water-soluble nature of the water-soluble hydrolyzed clinoptilolite fragments provides certain benefits and advantages when administering the water-soluble hydrolyzed clinoptilolite fragments. For example, oral administration of the water-soluble hydrolyzed clinoptilolite fragments can result in GI absorption of at least a portion of the water-soluble hydrolyzed clinoptilolite fragments. The absorbed water-soluble hydrolyzed clinoptilolite fragments can pass into the blood and be transported to various parts of the body to provide various benefits and advantages. Non-limiting examples of such benefits include: binding heavy metals/environmental toxins for detoxification; absorption at the cellular level; passing into adipose tissue, where heavy metals can accumulate or can be stored within adipose tissue; reduction of reactive oxygen species and inflammation related thereto; providing an increase in energy; and providing an increase in one or more of focus, concentration, and memory.

The water-soluble hydrolyzed clinoptilolite fragments can be used alone and can be used as a component in various compositions that include one or more various dietary supplements, such as one or more various vitamins and/or one or more various nutraceuticals. Non-limiting examples of dietary supplements further include vitamins, minerals, fiber, fatty acids, amino acids, herbs, herbal extracts, and combinations thereof. The dietary supplement can include a water-soluble vitamin, such as one or more of vitamin $B_1$, vitamin $B_2$, vitamin $B_3$, vitamin $B_5$, vitamin $B_6$, vitamin $B_7$, vitamin $B_9$, vitamin $B_{12}$, vitamin D, and vitamin C. In certain embodiments, such dietary supplements are not intended to diagnose, treat, cure, or prevent any disease. The water-soluble hydrolyzed clinoptilolite fragments can also be used to chelate or scavenge various metals, including toxic metals, where the water-soluble hydrolyzed clinoptilolite fragments can facilitate detoxification.

In certain embodiments, the water-soluble hydrolyzed clinoptilolite fragments can be combined with vitamin C (i.e., ascorbic acid), including various salts, derivatives, and esters thereof. Vitamin C receptors exist in the GI tract and in endothelial cells of various tissues in the human body. Examples include the GLUT1 receptor for uptake of vitamin C as well as glucose. Uptake can therefore occur in the GI tract and across blood vessels. For example, the number of vitamin C receptors can be significantly increased in endothelial cells that are part of the blood-brain barrier. As shown by LC-MS of the water-soluble hydrolyzed clinoptilolite fragments, at least one sodium ion is associated with each of the various molecular weight species of the hydrolyzed clinoptilolite fragments. Thus, the combination of vitamin C with water-soluble hydrolyzed clinoptilolite fragments can provide [hydrolyzed clinoptilolite fragment]-[sodium]-[ascorbic acid] salt. A composition including water-soluble hydrolyzed clinoptilolite fragments and vitamin C can therefore provide a complex between individual water-soluble hydrolyzed clinoptilolite fragments and vitamin C molecule, where an ionic bond can be formed between the sodium ion associated with a water-soluble hydrolyzed clinoptilolite fragment and vitamin C. In this way, the ionically bonded vitamin C molecule can serve as a "targeting device" for cells displaying vitamin C receptors. Such cells can bind the vitamin C molecule complexed with the water-soluble hydrolyzed clinoptilolite fragment and carry the water-soluble hydrolyzed clinoptilolite fragment along during uptake of the vitamin C molecule. One embodiment includes a solution of water-soluble hydrolyzed clinoptilolite fragments combined with vitamin C having the following characteristics: pH of 3.0-4.5; water-soluble hydrolyzed clinoptilolite fragments at 0.35-0.90 mg/mL; vitamin C at 3.5-6.0 mg/mL.

Benefits and advantages of water-soluble hydrolyzed clinoptilolite fragments in combination with vitamin C include the following non-limiting examples: detoxification of heavy metals/environmental toxins; increased absorption at the cellular level; passing into adipose tissue, where heavy metals can accumulate or can be stored within adipose tissue; reducing heavy metals related to inflammation; reducing reactive oxygen species related to inflammation; penetration of the blood-brain barrier; reducing heavy metals related inflammation in the central nervous system (CNS); reducing reactive oxygen species related inflammation in the CNS; providing an increase in energy; and providing an increase in one or more of focus, concentration, and memory.

In certain embodiments, the water-soluble hydrolyzed clinoptilolite fragments can be combined with vitamin C and other components, including one or more sleep aids. Examples of sleep aids include L-tryptophan and Alphawave® Calming Blend (commercially available from Ethical Naturals Inc., where Alphawave® Calming Blend includes optionally purified L-theanine, and herbal extracts of chamomile, lemon balm, passion flower, hops, and valerian). Formulations including one or more sleep aids can be used to improve the initiation and/or maintenance of sleep. The initiation and maintenance of sleep can be related with the production, release, and blood concentration levels of melatonin according to the following pathway:

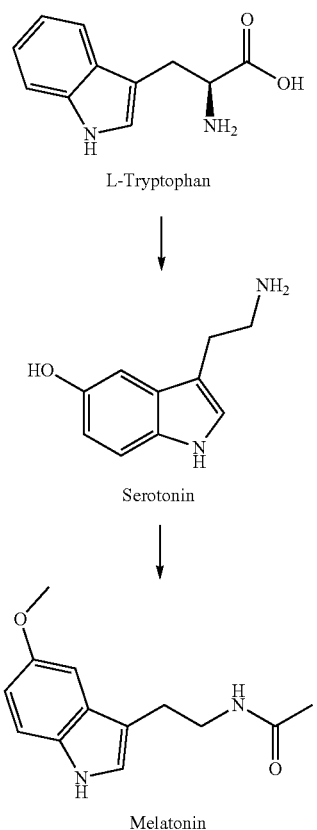

L-Tryptophan

Serotonin

Melatonin

In the brain, serotonin biosynthesis can depend on the quantity of tryptophan, which crosses the blood-brain barrier. L-theanine (an ingredient of Alphawave® Calming Blend) is an amino acid found in green tea leaves and can function as a natural relaxant. Formulation embodiments can include: water-soluble hydrolyzed clinoptilolite fragments at 0.35-4.5 mg/ml; vitamin-C at 3.5-6.0 mg/ml; L-tryptophan at 1.0-4.0 mg/ml; and Alphawave® Calming Blend at 10-50 mg/ml. Benefits and advantages include the following non-limiting examples: absorption at the cellular level; penetration of the blood-brain barrier; supports smooth initiation and/or maintenance of sleep; supports relaxation without drowsiness; reduces nervous tension; and sustains a sense of calm with focused energy, without forced spikes and crashes.

A composition including the water-soluble hydrolyzed clinoptilolite fragments can be formulated in various ways, typically for oral administration. Examples include forming the composition into one or more various aqueous solutions, liquid capsules, providing the composition in a liquid or slurry form, and providing the composition as a gel or syrup. The water-soluble hydrolyzed clinoptilolite fragments can also be dried (e.g., lyophilized) or partially dried and provided in a solid or partially solid form, such as a powder or paste. Composition components can be entirely admixed together into a single portion, each provided as a separate portion, or various components can be admixed where the whole composition is provided by more than one portion but where a total number of portions is less than the number of components. Other dosage forms suitable for oral administration can be used. In some embodiments, the water-soluble hydrolyzed clinoptilolite fragments can be formulated for other routes of administration, such as sublingual, rectal, topical, intranasal, inhalation, and ophthalmic routes.

Other components can be included in the composition, such as various excipients, including one or more antiadherents (e.g., magnesium stearate), binders (e.g., saccharides, gelatin, polymers), coatings (e.g., hydroxypropyl methylcellulose, enterics such as waxes, plastics, fibers etc.), disintegrants (e.g., polyvinylpyrrolidone, carboxymethyl cellulose, modified starches), flavors, colors, lubricants (e.g., talc, silica, fats), glidants (e.g., fumed silica, talc, magnesium carbonate), sorbents, preservatives (e.g., antioxidants such as vitamins A, E, and C; sodium benzoate; potassium sorbate), and sweeteners.

EXAMPLES

The following protocol was used to produce water-soluble hydrolyzed clinoptilolite fragments by hydrolyzing zeolite.

A hydrolysis reaction was assembled as follows, where the reaction mixture included 1 molar zeolite clinoptilolite and 0.16 molar phosphoric acid in UV Treated R/O water.
1. A stainless steel pot was placed over a heating plate.
2. Filtered and UV Treated Reverse Osmosis water was added in the stainless steel pot and stirring was initiated.
3. Under constant stirring, 1 M of clinoptilolite was transferred slowly to the stainless steel pot.
4. The mixture of clinoptilolite-water was heated to 170-175° F. (77-79° C.)
5. 0.16 M of phosphoric acid (85%) was added to the clinoptilolite-water mixture under constant stirring. This time-point of the hydrolysis reaction was time-point zero.
6. Under constant stirring the mixture was further heated to 170-175° F. (77-79° C.) as needed for the completion of the hydrolysis reaction.
7. Once the hydrolysis reaction was completed, stirring and heating stopped. The stainless steel pot with the mixture was immediately removed from the heating plate surface and left to cool at room temperature for 24 hours.

At various time intervals after time-point zero, such as every hour, half-hour, or quarter-hour, stirring and heating of the reaction mixture can be stopped. Morphology of the mixture surface can be observed. Heating and stirring of the reaction mixture can be continued if the hydrolysis reaction is not yet complete. The hydrolysis reaction and monitoring thereof can be continued.

Siphoning and filtering of the hydrolysis reaction product included the following aspects.
1. The reaction mixture was cooled at room temperature.
2. Two distinct layers were formed in the pot as the result of the hydrolysis reaction—a liquid layer and a solid layer.
3. Siphoning of the liquid layer was performed.
4. Filtration of the liquid product was performed as needed to collect a transparent liquid with light yellowish tint.
5. The liquid product was placed in a refrigerator.

Quantitative characteristics of the hydrolysis reaction product in the liquid layer included a pH of 4.0-5.5 and a solids content of 15-21 mg/ml. The amount of water-soluble hydrolyzed clinoptilolite fragments in the liquid layer, or the solids content, was determined by placing a certain volume of the hydrolysis reaction (e.g., 30-50 ml) on an evaporating plate and allowing to dry in a warm chamber at 60° C. for 24 hours. The amount of residual solids was measured once the liquid placed in the evaporating plate was fully evaporated.

Analytical chemistry testing for water-soluble hydrolyzed clinoptilolite fragments included the following. Liquid chromatography with mass spectrometry (LC-MS) was performed to test the successful transformation of the non-water-soluble zeolite clinoptilolite to water-soluble clinoptilolite fragments. LC-MS confirmed that the result of the zeolite clinoptilolite hydrolysis as described above resulted in an aqueous solution of water-soluble zeolite clinoptilolite derived fragments. LC-MS analysis was performed using an Agilent 1200 HPLC, an Agilent 6210 TOF Mass Spectrometer with Electrospray Ionization. The hydrolysis product was diluted in the mobile phase for analysis by direct injection mass spectrometry. The mobile phase consisted of 50/50 acetonitrile/water with 0.1% formic acid. The sample was injected into the mobile phase stream, which was electrosprayed into the TOF mass spectrometer.

Six different preparations of water-soluble hydrolyzed clinoptilolite fragments were analyzed.

FIG. 1 shows a spectrogram for the first water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 2:
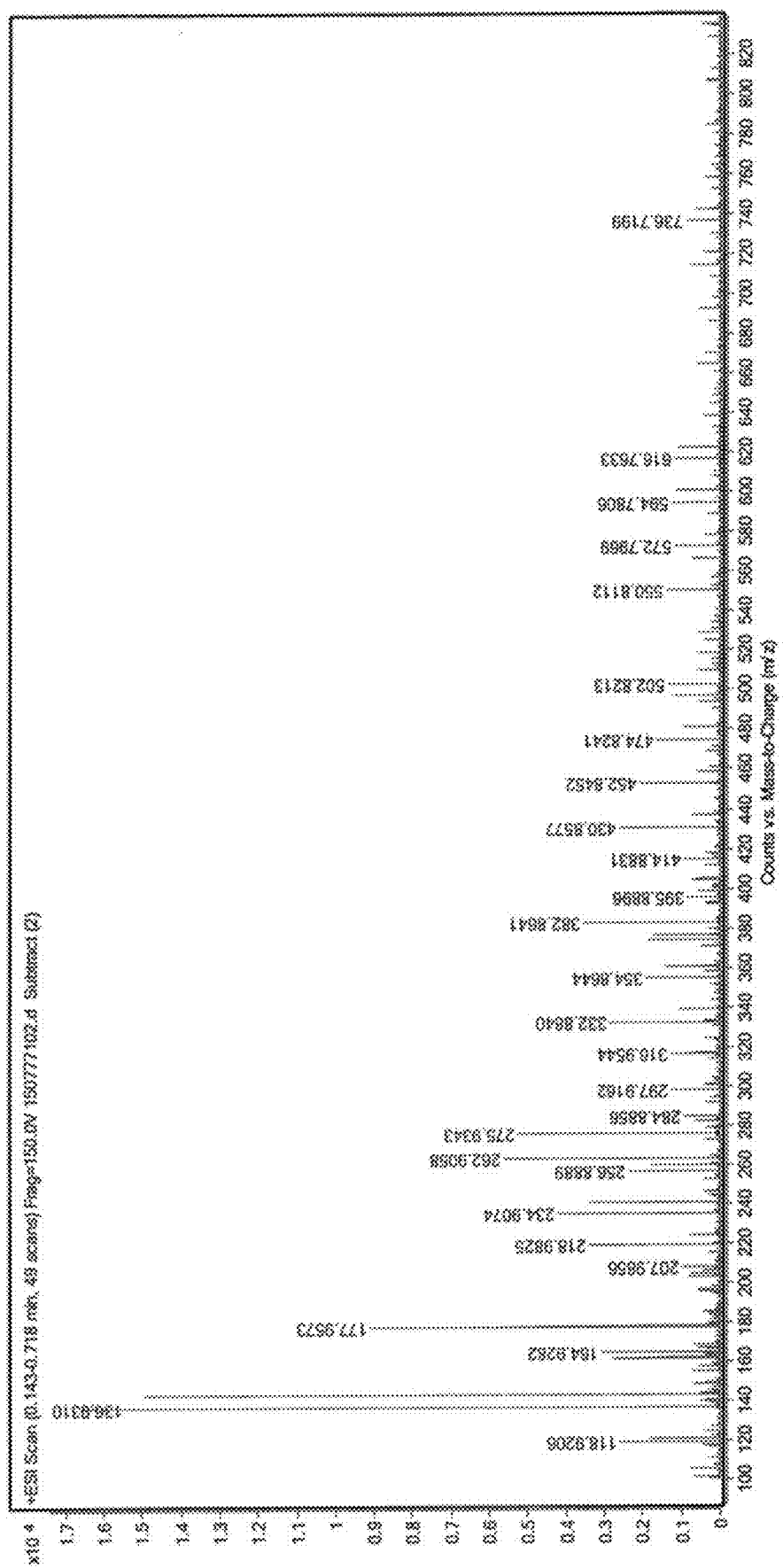
FIG. 2 depicts another spectrogram obtained from LC-MS analysis of another preparation of water-soluble hydrolyzed clinoptilolite fragments having a range of molecular weights between 100-820 Daltons produced according to the present technology.

FIG. 2 shows a spectrogram for the second water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 3:
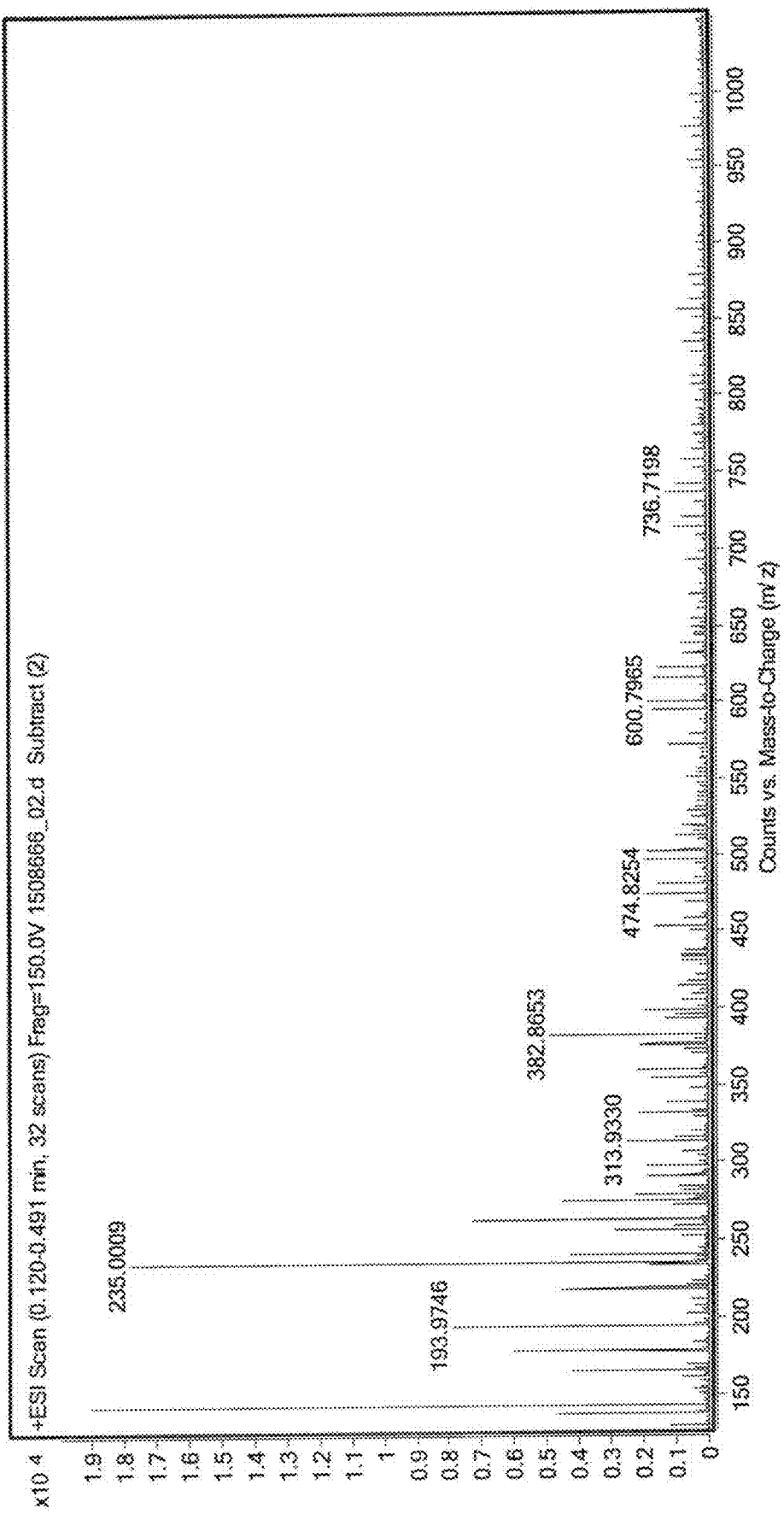
FIG. 3 depicts yet another spectrogram obtained from LC-MS analysis of yet another preparation of water-soluble hydrolyzed clinoptilolite fragments having a range of molecular weights between 100-1000 Daltons produced according to the present technology.

FIG. 3 shows a spectrogram for the third water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 4:
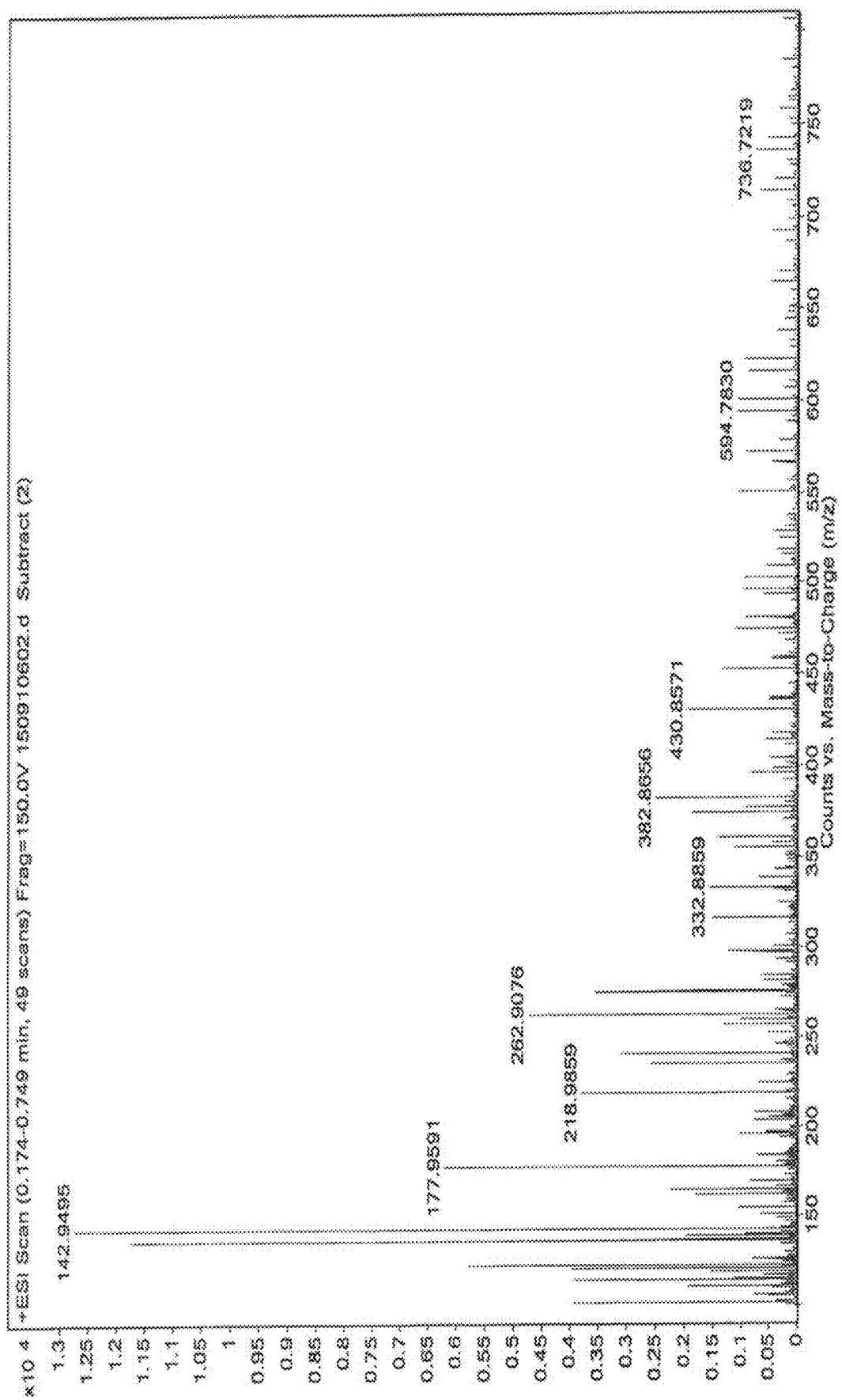
FIG. 4 depicts yet another spectrogram obtained from LC-MS analysis of yet another preparation of water-soluble hydrolyzed clinoptilolite fragments having a range of molecular weights between 100-800 Daltons produced according to the present technology.

FIG. 4 shows a spectrogram for the fourth water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 5:
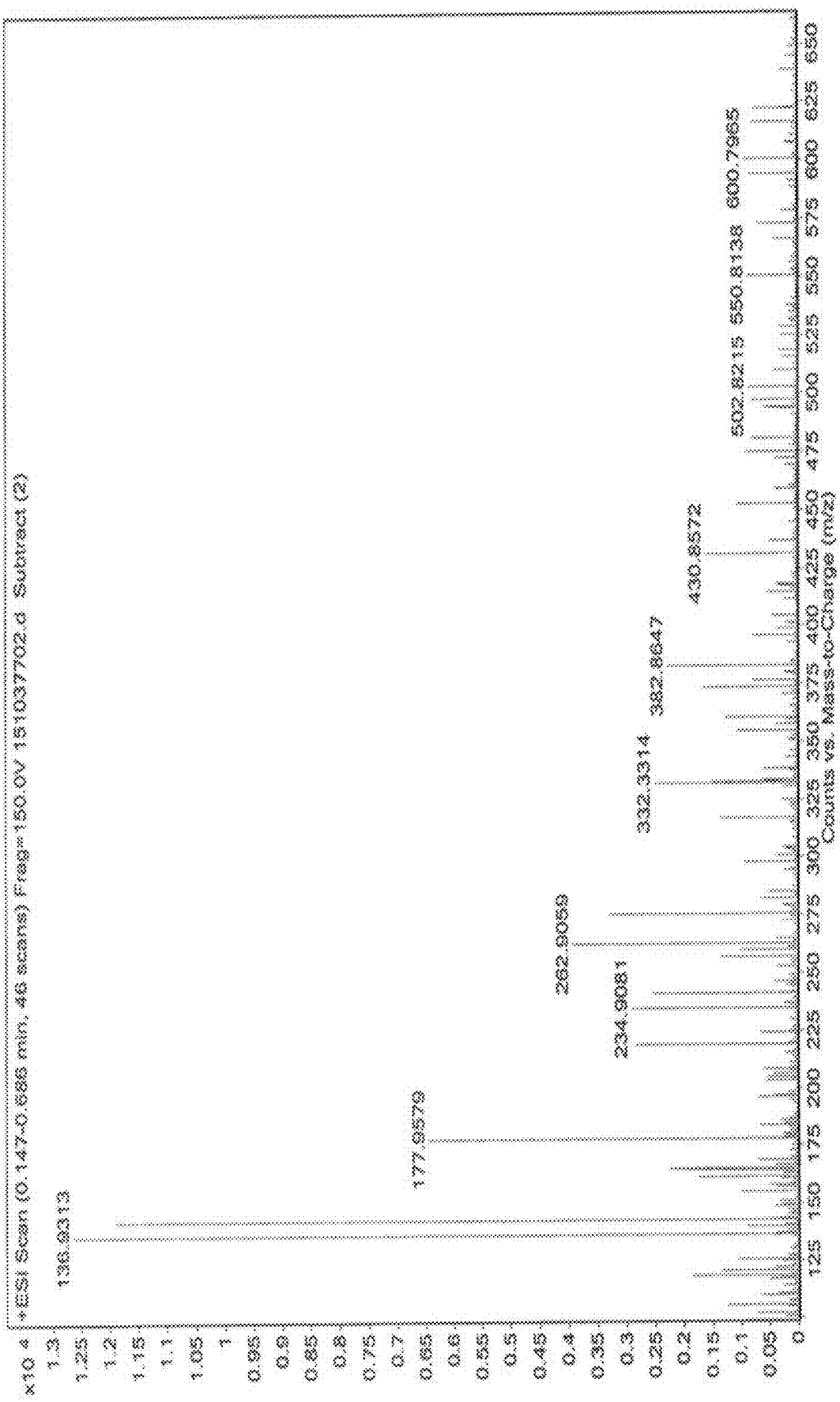
FIG. 5 depicts yet another spectrogram obtained from LC-MS analysis of yet another preparation of water-soluble hydrolyzed clinoptilolite fragments having a range of molecular weights between 100-650 Daltons produced according to the present technology.

FIG. 5 shows a spectrogram for the fifth water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 6:
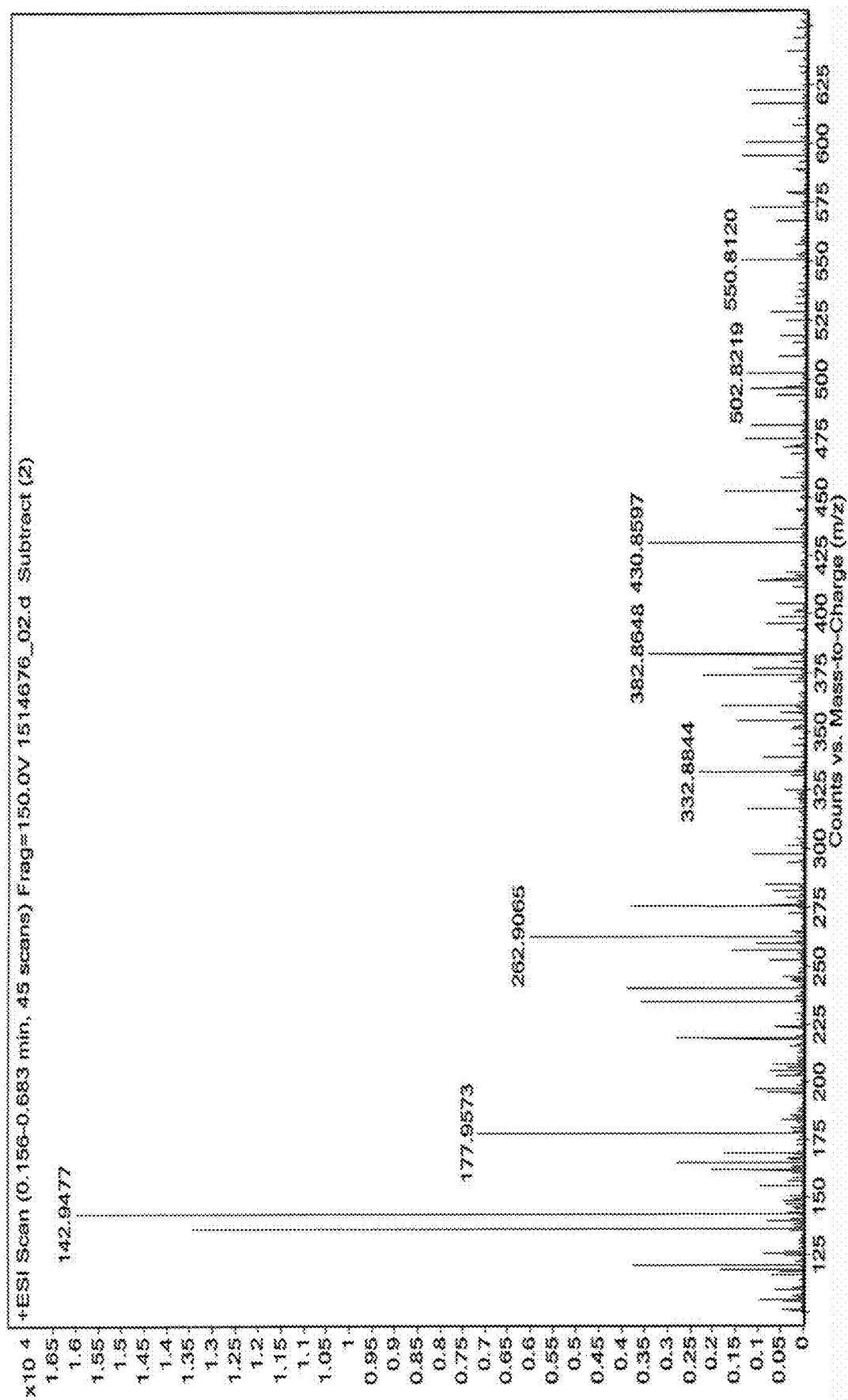
FIG. 6 depicts yet another spectrogram obtained from LC-MS analysis of yet another preparation of water-soluble hydrolyzed clinoptilolite fragments having a range of molecular weights between 100-650 Daltons produced according to the present technology.
Figure 7:
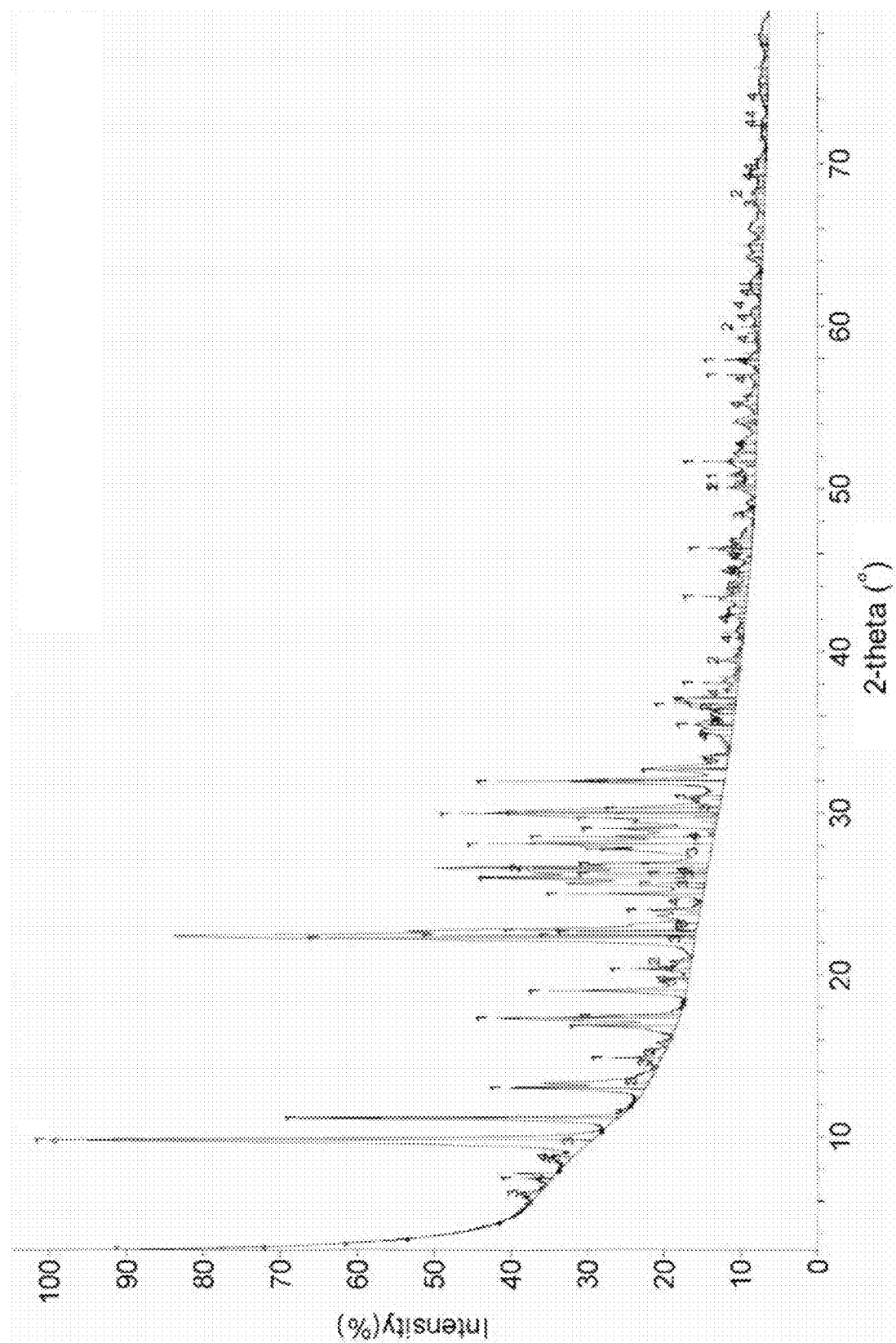
FIG. 7 depicts an X-ray diffraction (XRD) pattern for a starting zeolite clinoptilolite material according to another embodiment of the disclosure.
Figure 8:
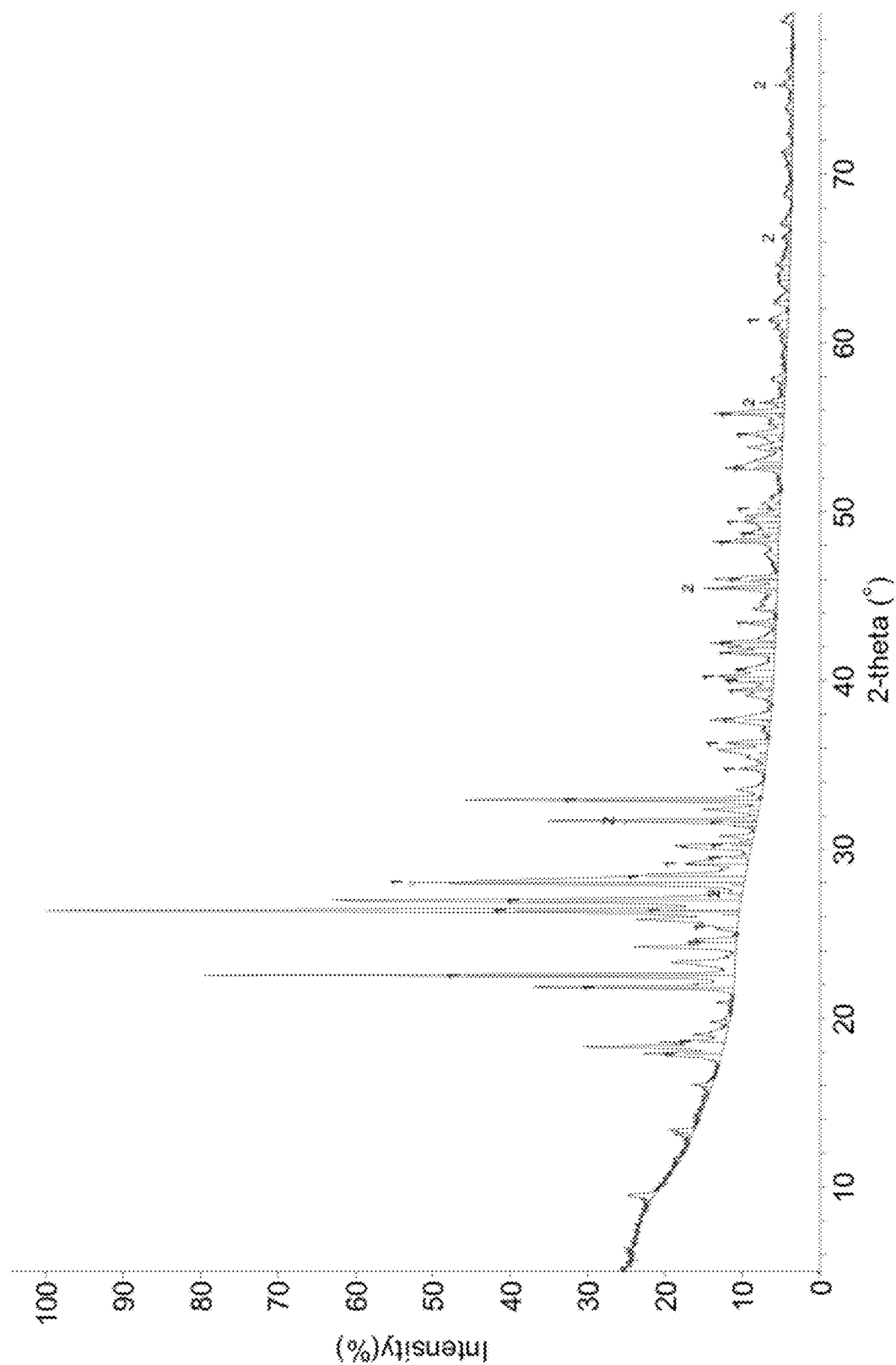
FIG. 8 depicts the XRD pattern for a first preparation of water-soluble hydrolyzed clinoptilolite fragments according to another embodiment of the disclosure.
Figure 9:
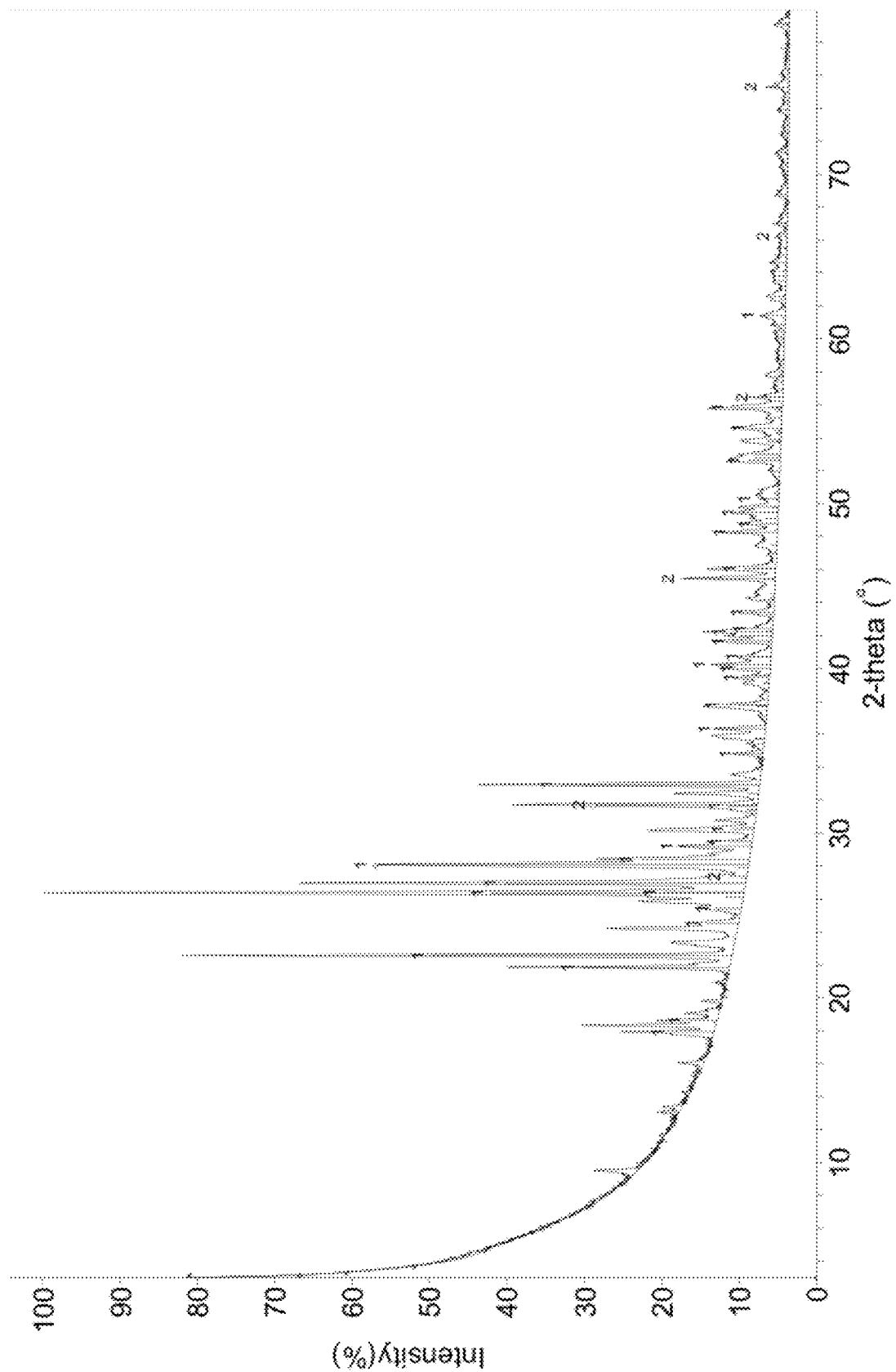
FIG. 9 depicts the XRD pattern for a second preparation of water-soluble hydrolyzed clinoptilolite fragments according to another embodiment of the disclosure.
Figure 10:
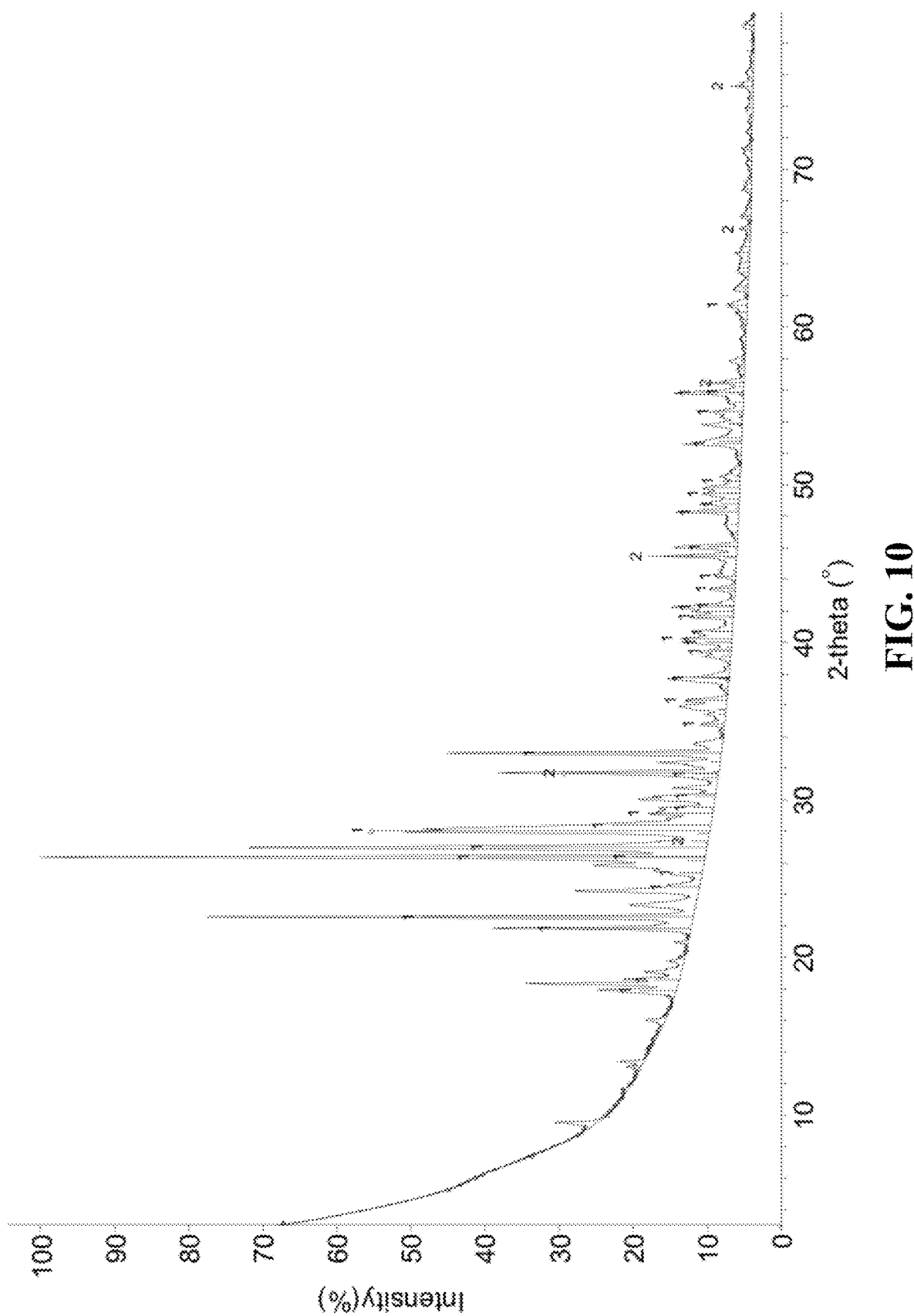
FIG. 10 depicts the XRD pattern for a third preparation of water-soluble hydrolyzed clinoptilolite fragments according to another embodiment of the disclosure.

FIG. 6 shows a spectrogram for the sixth water-soluble hydrolyzed clinoptilolite fragment preparation including species having a range of molecular weights between 100-1000 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected. Based upon the LC-MS data, the water-soluble hydrolyzed clinoptilolite fragments have molecular weights ranging between 100-1000 Daltons. The molecular weight of a unit cell of the starting zeolite clinoptilolite material is approximately 474 g/mol, where it is noted that individual unit cells can vary in chemical composition, especially with associated exchange cations. Therefore, the charged particles (i.e., the water-soluble hydrolyzed clinoptilolite fragments) separated by liquid chromatography, which were subsequently characterized by mass spectroscopy, appear to contain from 0.46 to 1.31 clinoptilolite unit cells. Without wishing to be bound by theory, it is believed that the water-soluble hydrolyzed clinoptilolite fragments include fragments of unit cells derived from the starting zeolite clinoptilolite, where the hydrolysis reaction has served to fragment the repeating unit cell structure of the zeolite clinoptilolite at various labile positions to give clinoptilolite fragments including complete unit cells, incomplete unit cells, and complete unit cells that remain coupled to remnants of formerly adjacent unit cells.

Alternatively, or in addition to, the water-soluble hydrolyzed clinoptilolite fragments can be distinguished by one or more characteristic peaks in the powder X-ray diffraction pattern at the unique values of 2theta as shown in FIGS. 7-10. For example, one or more unique 2theta values (in degrees) can provide a fingerprint and a way to identify the special hydrolysis products created using the present technology, as will be described further herein.

The present disclosure includes further characterization of the water-soluble hydrolyzed clinoptilolite fragments, including: particle size distribution (PSD) by use of electron scanning microscopy (ESM); free heavy metals levels analysis, using industry standard USP 232/233 procedures, to ascertain free heavy metals leached from the starting zeolite clinoptilolite to the water solution during the process of zeolite hydrolysis (to make sure that the "free" heavy metals concentration in the final water solution of water soluble hydrolyzed clinoptilolite fragments meets applicable safety standards), with the metals testing done with inductive coupled plasma-mass spectrometry (ICP-MS); pharmacokinetic data from parallel artificial membrane permeability assay (PAMPA) studies conducted on the product, and X-ray diffraction (XRD) testing.

The PSD testing included a particle size analysis to 0.1 μm minimum diameter of four aqueous suspensions of hydrolyzed clinoptilolite fragments prepared according the method of the present disclosure. Each sample consisted of 100 mL aqueous solution of hydrolyzed clinoptilolite fragments. Each sample was stored under refrigeration (2-8° C.). Each sample was removed from the refrigerator and allowed to stand overnight for equilibration to room temperature prior to sample preparation. Each sample was prepared for analysis in accordance with MVA SOP 310, "Sample Preparation Methods for Total Particle Sizing Using Microscopical Techniques." The zeolite crystals were prepared by filtration of 100 mL through a 0.1 µm pore size polycarbonate track etch membrane filter. The particle size distribution was measured in accordance with MVA SOP 316, "Automated Particle Size Analysis Using the JEOL JSM-6500F FESEM and Thermo Scientific Noran System 7" from digital images of the particles on the filters. The particle size data are presented in terms of particle number.

The size distributions of the particles down to 0.1 micrometer are shown in Table 3. Approximately 95% of the particles sized were less than 1 µm in diameter.

The results of the PSD testing are summarized below in Table 3.

TABLE 3

Diameter Range - PSD

| # | Diameter Range (µm) | Number - % | Mean | SD |
|---|---|---|---|---|
| 1 | 0.1-≤1.0 | 91-98 | 95.24 | 1.690 |
| 2 | >1.0-≤2.5 | 1-8 | 4.33 | 1.530 |
| 3 | >2.5-≤5.0 | 0-1 | 0.36 | 0.139 |
| 4 | >5.0-≤7.5 | 0-1 | 0.06 | 0.041 |
| 5 | >7.5-≤10.0 | 0-0.5 | 0.00 | 0.004 |
| 6 | >10.0 | 0-0.5 | 0.01 | 0.013 |
| | Total Particles | Number | 20.949 | 1.889 |

The results of the free heavy metals testing done with ICP-MS is shown below in Tables 4-5.

TABLE 4

Elemental Impurities Limits and Specifications.
Elemental Impurities Limits and Specifications

| # | | Element | Limit | Unit | Specification |
|---|---|---|---|---|---|
| 1 | Al | Aluminum | N/A | ppm | N/A |
| 2 | Sb | Antimony | ≤1,200 | ug/serving | USP <232> |
| 3 | As | Arsenic | ≤15 | ug/serving | USP <232> |
| 4 | Ba | Barium | ≤1,400 | ug/serving | USP <232> |
| 5 | Be | Beryllium | N/A | ppm | N/A |
| 6 | Bi | Bismuth | N/A | ppm | N/A |
| 7 | B | Boron | N/A | ppm | N/A |
| 8 | Cd | Cadmium | ≤5 | ug/serving | USP <232> |
| 9 | Ca | Calcium | N/A | ppm | N/A |
| 10 | Ce | Cerium | N/A | ppm | N/A |
| 11 | Cs | Cesium | N/A | ppm | N/A |
| 12 | Cr | Chromium | ≤11,000 | ug/serving | USP <232> |
| 13 | Co | Cobalt | ≤50 | ug/serving | USP <232> |
| 14 | Cu | Copper | ≤3,000 | ug/serving | USP <232> |
| 15 | Dy | Dysprosium | N/A | ppm | N/A |
| 16 | Er | Erbium | N/A | ppm | N/A |
| 17 | Eu | Europium | N/A | ppm | N/A |
| 18 | Gd | Gadolinium | N/A | ppm | N/A |
| 19 | Ga | Gallium | N/A | ppm | N/A |
| 20 | Ge | Germanium | N/A | ppm | N/A |
| 21 | Au | Gold | ≤100 | ug/serving | USP <232> |
| 22 | Hf | Hafnium | N/A | ppm | N/A |
| 23 | Ho | Holmium | N/A | ppm | N/A |
| 24 | In | Indium | N/A | ppm | N/A |
| 25 | Ir | Iridium | ≤100 | ug/serving | USP <232> |
| 26 | Fe | Iron | N/A | ppm | N/A |
| 27 | La | Lanthanum | N/A | ppm | N/A |
| 28 | Pb | Lead | ≤5 | ug/serving | USP <232> |
| 29 | Li | Lithium | ≤550 | ug/serving | USP <232> |
| 30 | Lu | Lutetium | N/A | ppm | N/A |
| 31 | Mg | Magnesium | N/A | ppm | N/A |
| 32 | Mn | Manganese | N/A | ppm | N/A |
| 33 | Hg | Mercury | ≤30 | ug/serving | USP <232> |
| 34 | Mo | Molybdenum | ≤3,000 | ug/serving | USP <232> |
| 35 | Nd | Neodymium | N/A | ppm | N/A |
| 36 | Ni | Nickel | ≤200 | ug/serving | USP <232> |
| 37 | Nb | Niobium | N/A | ppm | N/A |

TABLE 4-continued

Elemental Impurities Limits and Specifications.
Elemental Impurities Limits and Specifications

| # | | Element | Limit | Unit | Specification |
|---|---|---|---|---|---|
| 38 | Os | Osmium | ≤100 | ug/serving | USP <232> |
| 39 | Pd | Palladium | ≤100 | ug/serving | USP <232> |
| 40 | P | Phosphorus | N/A | ppm | N/A |
| 41 | Pt | Platinum | ≤100 | ug/serving | USP <232> |
| 42 | K | Potassium | N/A | ppm | N/A |
| 43 | Pr | Praseodymium | N/A | ppm | N/A |
| 44 | Re | Rhenium | N/A | ppm | N/A |
| 45 | Rh | Rhodium | ≤100 | ug/serving | USP <232> |
| 46 | Rb | Rubidium | N/A | ppm | N/A |
| 47 | Ru | Ruthenium | ≤100 | ug/serving | USP <232> |
| 48 | Sm | Samarium | N/A | ppm | N/A |
| 49 | Sc | Scandium | N/A | ppm | N/A |
| 50 | Se | Selenium | ≤150 | ug/serving | USP <232> |
| 51 | Ag | Silver | ≤150 | ug/serving | USP <232> |
| 52 | Na | Sodium | N/A | ppm | N/A |
| 53 | Sr | Strontium | N/A | ppm | N/A |
| 54 | S | Sulfur | N/A | ppm | N/A |
| 55 | Ta | Tantalum | N/A | ppm | N/A |
| 56 | Te | Tellurium | N/A | ppm | N/A |
| 57 | Tb | Terbium | N/A | ppm | N/A |
| 58 | Tl | Thallium | ≤8 | ug/serving | USP <232> |
| 59 | Th | Thorium | N/A | ppm | N/A |
| 60 | Tm | Thulium | N/A | ppm | N/A |
| 61 | Sn | Tin | ≤6,000 | ug/serving | USP <232> |
| 62 | Ti | Titanium | N/A | ppm | N/A |
| 63 | W | Tungsten | N/A | ppm | N/A |
| 64 | U | Uranium | N/A | ppm | N/A |
| 65 | V | Vanadium | ≤100 | ug/serving | USP <232> |
| 66 | Yb | Ytterbium | N/A | ppm | N/A |
| 67 | Y | Yttrium | N/A | ppm | N/A |
| 68 | Zn | Zinc | N/A | ppm | N/A |
| 69 | Zr | Zirconium | N/A | ppm | N/A |

TABLE 5

HCF Specifications.
HCF Elemental Impurities Limits

| # | | Element | Limit | Unit |
|---|---|---|---|---|
| 1 | Al | Aluminum | <1.5 | ppm |
| 2 | Sb | Antimony | <0.075 | ug/serving |
| 3 | As | Arsenic | <0.5 | ug/serving |
| 4 | Ba | Barium | <0.075 | ug/serving |
| 5 | Be | Beryllium | <3 | ppm |
| 6 | Bi | Bismuth | <3 | ppm |
| 7 | B | Boron | <15 | ppm |
| 8 | Cd | Cadmium | <0.036 | ug/serving |
| 9 | Ca | Calcium | <1,000 | ppm |
| 10 | Ce | Cerium | <1.5 | ppm |
| 11 | Cs | Cesium | <1.5 | ppm |
| 12 | Cr | Chromium | <0.075 | ug/serving |
| 13 | Co | Cobalt | <0.075 | ug/serving |
| 14 | Cu | Copper | <0.075 | ug/serving |
| 15 | Dy | Dysprosium | <1.5 | ppm |
| 16 | Er | Erbium | <1.5 | ppm |
| 17 | Eu | Europium | <1.5 | ppm |
| 18 | Gd | Gadolinium | <1.5 | ppm |
| 19 | Ga | Gallium | <1.5 | ppm |
| 20 | Ge | Germanium | <1.5 | ppm |
| 21 | Au | Gold | <0.075 | ug/serving |
| 22 | Hf | Hafnium | <1.5 | ppm |
| 23 | Ho | Holmium | <1.5 | ppm |
| 24 | In | Indium | <1.5 | ppm |
| 25 | Ir | Iridium | <0.075 | ug/serving |
| 26 | Fe | Iron | <15 | ppm |
| 27 | La | Lanthanum | <1.5 | ppm |
| 28 | Pb | Lead | <0.0075 | ug/serving |
| 29 | Li | Lithium | <0.5 | ug/serving |
| 30 | Lu | Lutetium | <1.5 | ppm |
| 31 | Mg | Magnesium | <200 | ppm |
| 32 | Mn | Manganese | <15 | ppm |

TABLE 5-continued

HCF Specifications.
HCF Elemental Impurities Limits

| # | Element | | Limit | Unit |
|---|---|---|---|---|
| 33 | Hg | Mercury | <0.015 | ug/serving |
| 34 | Mo | Molybdenum | <0.075 | ug/serving |
| 35 | Nd | Neodymium | <1.5 | ppm |
| 36 | Ni | Nickel | <0.075 | ug/serving |
| 37 | Nb | Niobium | <1.5 | ppm |
| 38 | Os | Osmium | <0.075 | ug/serving |
| 39 | Pd | Palladium | <0.075 | ug/serving |
| 40 | P | Phosphorus | <10,000 | ppm |
| 41 | Pt | Platinum | <0.075 | ug/serving |
| 42 | K | Potassium | <140 | ppm |
| 43 | Pr | Praseodymium | <1.5 | ppm |
| 44 | Re | Rhenium | <1.5 | ppm |
| 45 | Rh | Rhodium | <0.075 | ug/serving |
| 46 | Rb | Rubidium | <1.5 | ppm |
| 47 | Ru | Ruthenium | <0.075 | ug/serving |
| 48 | Sm | Samarium | <1.5 | ppm |
| 49 | Sc | Scandium | <1.5 | ppm |
| 50 | Se | Selenium | <0.075 | ug/serving |
| 51 | Ag | Silver | <0.075 | ug/serving |
| 52 | Na | Sodium | <7000 | ppm |
| 53 | Sr | Strontium | <35 | ppm |
| 54 | S | Sulfur | <750 | ppm |
| 55 | Ta | Tantalum | <1.5 | ppm |
| 56 | Te | Tellurium | <1.5 | ppm |
| 57 | Tb | Terbium | <1.5 | ppm |
| 58 | Tl | Thallium | <0.075 | ug/serving |
| 59 | Th | Thorium | <1.5 | ppm |
| 60 | Tm | Thulium | <1.5 | ppm |
| 61 | Sn | Tin | <0.075 | ug/serving |
| 62 | Ti | Titanium | <1.5 | ppm |
| 63 | W | Tungsten | <1.5 | ppm |
| 64 | U | Uranium | <1.5 | ppm |
| 65 | V | Vanadium | <0.075 | ug/serving |
| 66 | Yb | Ytterbium | <5 | ppm |
| 67 | Y | Yttrium | <1.5 | ppm |
| 68 | Zn | Zinc | <1.5 | ppm |
| 69 | Zr | Zirconium | <1.5 | ppm |

Pharmacokinetic testing by PAMPA was also conducted. The assays were designed to determine the comparative flux of the water-soluble hydrolyzed clinoptilolite fragments using the µFLUX module of the uDISS Profiler™ apparatus at single load. Experimental details and protocols are summarized as follows.

The experiments were prepared using various pieces of laboratory equipment and supplies listed below.

Flux experiments were conducted using µFLUX glass donor/receiver (acceptor) pair glassware and µDISS Profiler™ (Pion Inc.) operated by AU Pro software (version 5.1). MB8 station with built-in stirring device (Pion Inc.), 9 mm cross-stir bars were used to provide sufficient mixing during dissolution-flux experiments.

The µDISS Profiler™ instrument used to quantify concentrations during the experiments employed up to eight photodiode array (PDA) spectrophotometers, each with its own dedicated fiber optic dip probe (FO), center-positioned in the vial holding 3-22 ml media. The concentration measurements were performed directly in the assay media, with processed results plotted in "real time." Interference due to background turbidity was minimized when needed by a spectral second derivative method.

Figure 11:
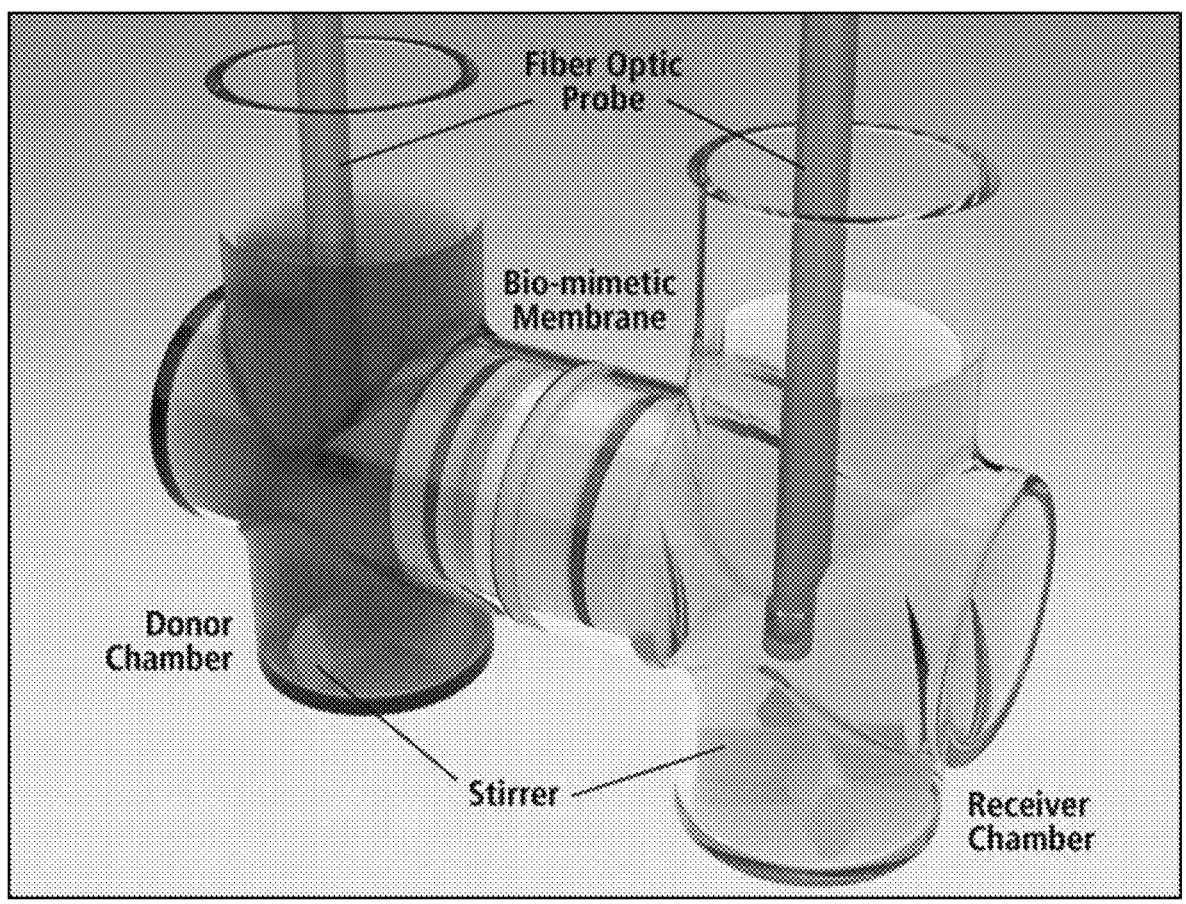
FIG. 11 is a schematic illustration showing a pair of donor (left) and receiver (or acceptor) (right) chambers separated by a bio-mimetic membrane, with fiber optic probes allowing simultaneous, real time concentration measurements in both chambers, for use in the Parallel Artificial Membrane Permeability Assay (PAMPA) of the water-soluble hydrolyzed clinoptilolite fragments.

The µFLUX™ device is an add-on option to the µDISS Profiler™ instrument consisting of four pairs of temperature controlled side-by-side permeability chambers mounted on top of the stirring platform. The device as shown in FIG. 11 was used in the study. Each pair consists of a donor and a receiver compartment separated by a filter-supported membrane. GIT-optimized artificial membrane (Double-Sink™ PAMPA2) was used in this study. The donor compartment is usually filled with 20 ml of the media of interest. For this study, the receiver compartment contained Acceptor Sink Buffer at pH 7.4 (ASB-7.4, Pion Inc). The integrated fiber-optic UV probes were positioned in the donor and receiver compartments allowing real time concentration monitoring in both chambers.

The flux (J) of a compound through a membrane is defined as the amount of compound crossing a unit area perpendicular to its flow per unit time. In the one-dimension steady-state approximation it may be expressed through the effective permeability coefficient and concentration of free compound c(t) in the donor compartment as follows.

$$J(t) = \frac{dm}{A \cdot dt} = P_e \cdot c(t)$$

In the µFLUX device, where area A is known and the rate of appearance of material (dm/dt) can be determined at any time point by continuously monitoring the concentration in the receiver (acceptor) compartment, the flux and its changes can be easily determined.

Figure 12:
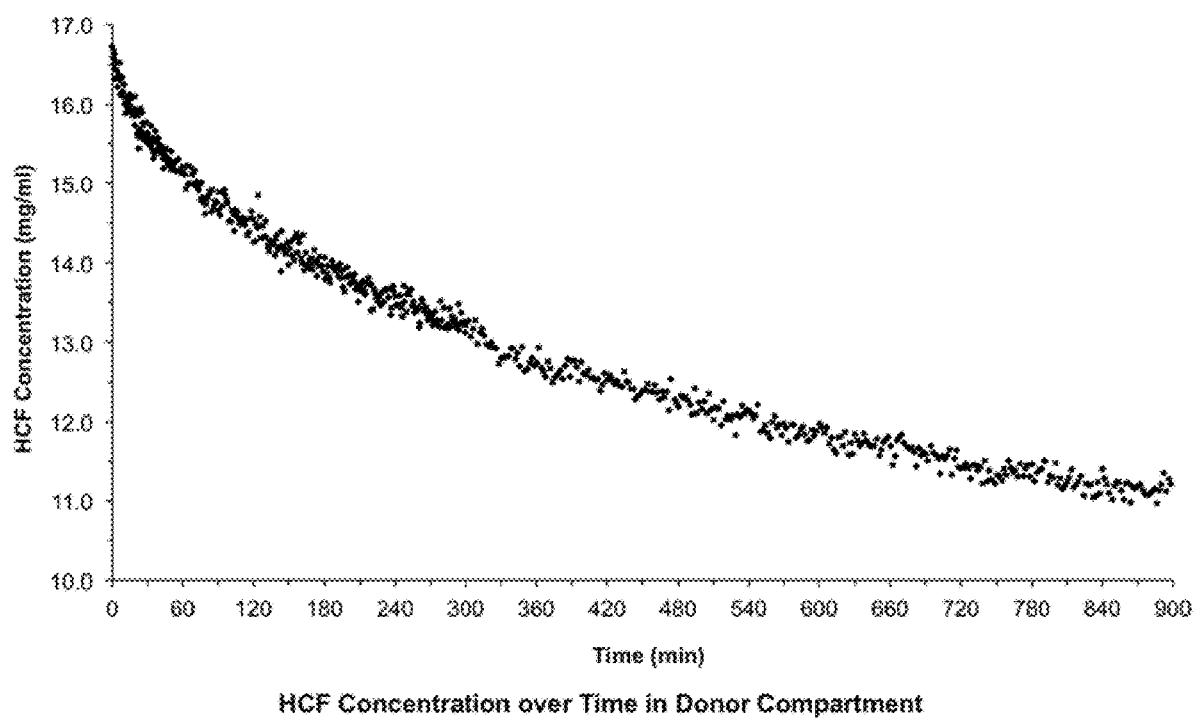
FIG. 12 is a concentration profile obtained via simultaneous, real time measurements for the water-soluble hydrolyzed clinoptilolite fragments in the donor chamber (left) shown in FIG. 11.
Figure 13:
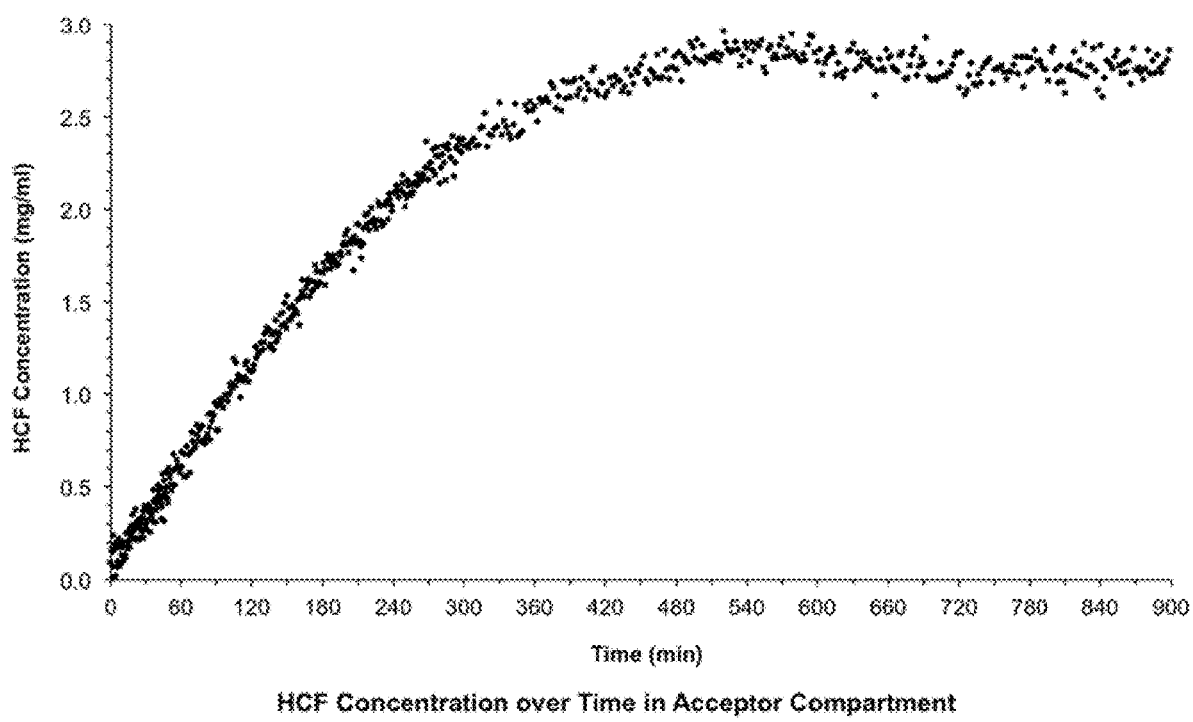
FIG. 13 is a concentration profile obtained via simultaneous, real time measurements for the water-soluble hydrolyzed clinoptilolite fragments in the receiver chamber (right) shown in FIG. 11.

Experimental samples and curves were then prepared, as shown in FIGS. 12 and 13. Aliquots (20 ml) of fresh solution containing the water soluble hydrolyzed clinoptilolite fragments were transferred into clean donor compartments of µFLUX assembled pairs. Aliquots (20 ml) of DI water (containing no water soluble hydrolyzed clinoptilolite fragments) were added to the donor and acceptor compartments of assembled µFLUX pairs reserved as a blank (Control). UV noise, characteristic for the assay was monitored within duration of the experiment.

All experiments were performed at room temperature at stirring conditions. The concentration monitoring in both compartments started immediately after addition of the sample and continued for more than 15 hours.

The results of the µFLUX experiments are summarized below in the Table 6.

TABLE 6

| Volume (mL) | Membrane Area (cm$^2$) | Slope in Receiver (mg/(mL*min)) | Flux (mg/(min*cm$^2$)) | Time interval (min) |
|---|---|---|---|---|
| 20 | 1.54 | 0.010 | 0.130 | 10-200 |

Flux – the slope of the concentration – time profile mg/(ml *min) was multiplied by the volume of receiver (20 ml) and divided by the area of the membrane (1.54 cm$^2$ Concentration profiles obtained in the donor and the acceptor compartments are shown in the FIGS. 12 and 13. These profiles show a reduction in the concentration in the donor compartment and an increase in the concentration in the receiver compartment.

Figure 14:
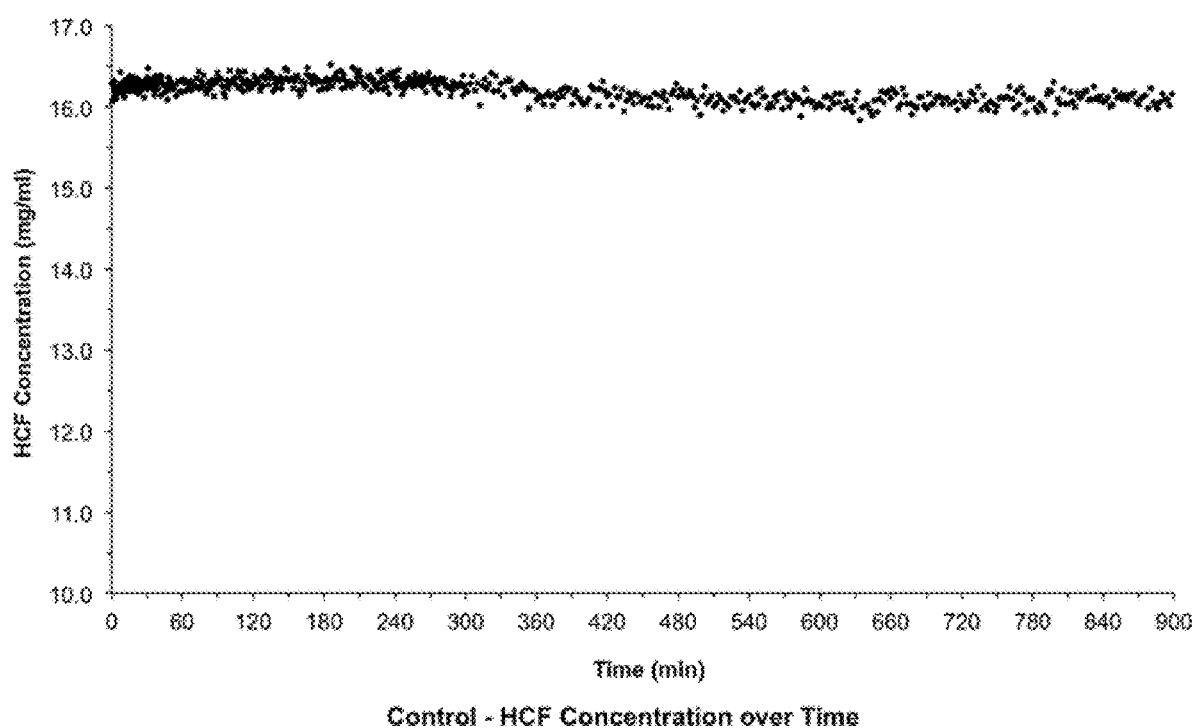
FIG. 14 is a concentration profile obtained via simultaneous, real time measurements for a control sample of water-soluble hydrolyzed clinoptilolite fragments.

In order to prove that the reduction of the concentration in the donor compartments reflected an actual kinetic process during Flux experiment and was not caused by artifacts or degradation of the sample an additional experiment was designed (herein referred as "control" assay). Aliquots (20 ml) of fresh solution of the hydrolyzed clinoptilolite fragments were transferred into clean glass vials and concentration of the sample was monitored within time interval similar to the duration of Flux experiment. No change in concentration of the sample was detected, as shown in FIG. 14.

Accordingly, based on the PAMPA testing detailed hereinabove, it is believed that the hydrolyzed clinoptilolite fragments prepared according to the present disclosure are able to, in vivo, cross cellular membranes.

The XRD pattern for the water-soluble hydrolyzed clinoptilolite fragments can provide a fingerprint and a way to identify the special hydrolysis products created using the present technology. For example, XRD peaks unique to the water-soluble hydrolyzed clinoptilolite fragments that are absent from the starting zeolite can provide a defining attribute of the water-soluble hydrolyzed clinoptilolite fragments. One or more of these peaks can be used to define or identify the water-soluble hydrolyzed clinoptilolite fragments produced by the hydrolysis reaction described herein and distinguish the hydrolyzed clinoptilolite fragments from the starting zeolite clinoptilolite material. The water-soluble hydrolyzed clinoptilolite fragments can therefore be distinguished by one or more characteristic peaks in the X-ray diffraction pattern. The XRD test results are shown below in Tables 7-11, and in FIGS. 7-10. The XRD testing was performed according to: (1) USP <941>; (2) BS EN 13925-3:2005 and (3) 21CFR Part 11.

TABLE 7

Test Results for the starting zeolite clinoptilolite.
Starting zeolite clinoptilolite

| # | 2 Θ | d(Å) | Intensity (%) |
|---|---|---|---|
| 1 | 6.496 | 13.596 | 3.8 |
| 2 | 7.462 | 11.838 | 2.9 |
| 3 | 7.729 | 11.43 | 8.1 |
| 4 | 8.752 | 10.096 | 5 |
| 5 | 9.837 | 8.984 | 100 |
| 6 | 11.174 | 7.912 | 59.3 |
| 7 | 11.689 | 7.565 | 2.3 |
| 8 | 13.032 | 6.788 | 20.5 |
| 9 | 13.33 | 6.637 | 19.7 |
| 10 | 13.93 | 6.352 | 3 |
| 11 | 14.902 | 5.94 | 5.5 |
| 12 | 15.3 | 5.787 | 2.5 |
| 13 | 15.869 | 5.58 | 2.6 |
| 14 | 16.363 | 5.413 | 2 |
| 15 | 16.589 | 5.34 | 4.8 |
| 16 | 16.908 | 5.24 | 18.1 |
| 17 | 17.309 | 5.119 | 32.7 |
| 18 | 17.521 | 5.058 | 9.4 |
| 19 | 19.062 | 4.652 | 19.1 |
| 20 | 19.663 | 4.511 | 5.5 |
| 21 | 20.416 | 4.347 | 9.6 |
| 22 | 20.834 | 4.26 | 4 |
| 23 | 22.421 | 3.962 | 96.1 |
| 24 | 22.721 | 3.91 | 53.5 |
| 25 | 23.138 | 3.841 | 12.5 |
| 26 | 23.658 | 3.758 | 7.7 |
| 27 | 24.026 | 3.701 | 9 |
| 28 | 25.061 | 3.55 | 18 |
| 29 | 25.68 | 3.466 | 25.8 |
| 30 | 26.063 | 3.416 | 41.1 |
| 31 | 26.298 | 3.386 | 32.5 |
| 32 | 26.632 | 3.344 | 50.5 |
| 33 | 26.832 | 3.32 | 22.5 |
| 34 | 27.703 | 3.218 | 15.1 |
| 35 | 27.77 | 3.21 | 23.5 |
| 36 | 27.851 | 3.201 | 17.9 |
| 37 | 27.954 | 3.189 | 20.4 |
| 38 | 28.004 | 3.184 | 24.5 |
| 39 | 28.153 | 3.167 | 34.2 |
| 40 | 28.571 | 3.122 | 17.6 |
| 41 | 29.039 | 3.073 | 16.9 |
| 42 | 29.439 | 3.032 | 15.7 |
| 43 | 30.024 | 2.974 | 42.4 |
| 44 | 30.943 | 2.888 | 7.2 |
| 45 | 31.964 | 2.798 | 29.2 |
| 46 | 32.732 | 2.734 | 14.5 |
| 47 | 33.467 | 2.675 | 5.2 |
| 48 | 35.054 | 2.558 | 6 |
| 49 | 35.488 | 2.528 | 7.5 |

TABLE 7-continued

Test Results for the starting zeolite clinoptilolite.
Starting zeolite clinoptilolite

| # | 2 Θ | d(Å) | Intensity (%) |
|---|---|---|---|
| 50 | 36.091 | 2.487 | 4.5 |
| 51 | 36.693 | 2.447 | 8.8 |
| 52 | 36.993 | 2.428 | 11 |
| 53 | 38.164 | 2.356 | 3.2 |
| 54 | 39.434 | 2.283 | 3.8 |
| 55 | 41.338 | 2.182 | 1.7 |
| 56 | 42.309 | 2.135 | 3.7 |
| 57 | 43.244 | 2.091 | 5.4 |
| 58 | 43.996 | 2.057 | 3 |
| 59 | 44.948 | 2.015 | 5.3 |
| 60 | 45.717 | 1.983 | 3.7 |
| 61 | 46.35 | 1.957 | 6.3 |
| 62 | 46.803 | 1.94 | 4.2 |
| 63 | 48.507 | 1.875 | 3 |
| 64 | 49.191 | 1.851 | 1.7 |
| 65 | 50.045 | 1.821 | 4.7 |
| 66 | 50.898 | 1.793 | 4.8 |
| 67 | 51.699 | 1.767 | 5.3 |
| 68 | 52.233 | 1.75 | 4.3 |
| 69 | 52.768 | 1.733 | 3.3 |
| 70 | 54.239 | 1.69 | 4.2 |
| 71 | 55.225 | 1.662 | 3.1 |
| 72 | 55.66 | 1.65 | 2.7 |
| 73 | 56.879 | 1.618 | 1.7 |
| 74 | 57.832 | 1.593 | 3 |
| 75 | 59.256 | 1.558 | 1.1 |
| 76 | 59.939 | 1.542 | 1.9 |

TABLE 8

Hydrolyzed Clinoptilolite Fragments XRD Peaks based on Intensity > 5%
HCF XRD Peaks (based on peaks with intensity > 5%)

| # | 2 Θ |
|---|---|
| 1 | 17.7 ± 0.2 |
| 2 | 17.9 ± 0.2 |
| 3 | 18.3 ± 0.2 |
| 4 | 18.6 ± 0.2 |
| 5 | 21.8 ± 0.2 |
| 6 | 22.0 ± 0.2 |
| 7 | 22.5 ± 0.2 |
| 8 | 23.3 ± 0.2 |
| 9 | 24.2 ± 0.2 |
| 10 | 25.9 ± 0.2 |
| 11 | 26.3 ± 0.2 |
| 12 | 26.9 ± 0.2 |
| 13 | 28.0 ± 0.2 |
| 14 | 28.5 ± 0.2 |
| 15 | 29.1 ± 0.2 |
| 16 | 29.4 ± 0.2 |
| 17 | 30.1 ± 0.2 |
| 18 | 30.2 ± 0.2 |
| 19 | 31.7 ± 0.2 |
| 20 | 32.3 ± 0.2 |
| 21 | 32.9 ± 0.2 |
| 22 | 35.9 ± 0.2 |
| 23 | 36.3 ± 0.2 |
| 24 | 37.6 ± 0.2 |
| 25 | 40.0 ± 0.2 |
| 26 | 40.2 ± 0.2 |
| 27 | 41.6 ± 0.2 |
| 28 | 41.9 ± 0.2 |
| 29 | 42.2 ± 0.2 |
| 30 | 45.4 ± 0.2 |
| 31 | 46.0 ± 0.2 |
| 32 | 48.2 ± 0.2 |
| 33 | 48.7 ± 0.2 |
| 34 | 49.4 ± 0.2 |
| 35 | 49.7 ± 0.2 |
| 36 | 52.5 ± 0.2 |
| 37 | 53.8 ± 0.2 |

TABLE 8-continued

Hydrolyzed Clinoptilolite Fragments XRD Peaks based on Intensity > 5%
HCF XRD Peaks (based on peaks with intensity > 5%)

| # | 2 Θ |
|---|---|
| 38 | 54.6 ± 0.2 |
| 39 | 55.8 ± 0.2 |

TABLE 9

Hydrolyzed Clinoptilolite Fragments XRD Peaks based on Intensity > 10%
HCF XRD Peaks (based on peaks with intensity > 10%)

| # | 2 Θ |
|---|---|
| 1 | 17.9 ± 0.2 |
| 2 | 18.3 ± 0.2 |
| 3 | 21.8 ± 0.2 |
| 4 | 22.5 ± 0.2 |
| 5 | 24.2 ± 0.2 |
| 6 | 25.9 ± 0.2 |
| 7 | 26.3 ± 0.2 |
| 8 | 26.9 ± 0.2 |
| 9 | 28.0 ± 0.2 |
| 10 | 30.1 ± 0.2 |
| 11 | 31.7 ± 0.2 |
| 12 | 32.9 ± 0.2 |
| 13 | 45.4 ± 0.2 |
| 14 | 55.8 ± 0.2 |

TABLE 10

Hydrolyzed Clinoptilolite Fragments XRD Peaks based on Intensity > 15%
HCF XRD Peaks (based on peaks with intensity > 15%)

| # | 2 Θ |
|---|---|
| 1 | 18.3 ± 0.2 |
| 2 | 21.8 ± 0.2 |
| 3 | 22.5 ± 0.2 |
| 4 | 24.2 ± 0.2 |
| 5 | 26.3 ± 0.2 |
| 6 | 26.9 ± 0.2 |
| 7 | 28.0 ± 0.2 |
| 8 | 31.7 ± 0.2 |
| 9 | 32.9 ± 0.2 |

TABLE 11

Hydrolyzed Clinoptilolite Fragments XRD Characteristic Peaks
HCF characteristic peaks

| # | 2 Θ |
|---|---|
| 1 | 9.7 ± 0.2 |
| 2 | 11.6 ± 0.2 |
| 3 | 13.0 ± 0.2 |
| 4 | 13.3 ± 0.2 |
| 5 | 17.7 ± 0.2 |
| 6 | 19.0 ± 0.2 |
| 7 | 20.8 ± 0.2 |
| 8 | 22.4 ± 0.2 |
| 9 | 23.1 ± 0.2 |
| 10 | 24.2 ± 0.2 |
| 11 | 25.9 ± 0.2 |
| 12 | 26.3 ± 0.2 |
| 13 | 26.9 ± 0.2 |
| 14 | 28.0 ± 0.2 |
| 15 | 28.5 ± 0.2 |
| 16 | 29.1 ± 0.2 |
| 17 | 29.4 ± 0.2 |
| 18 | 30.1 ± 0.2 |
| 19 | 30.9 ± 0.2 |

TABLE 11-continued

Hydrolyzed Clinoptilolite Fragments XRD Characteristic Peaks
HCF characteristic peaks

| # | 2 Θ |
|---|---|
| 20 | 31.9 ± 0.2 |
| 21 | 32.9 ± 0.2 |
| 22 | 33.4 ± 0.2 |
| 23 | 35.4 ± 0.2 |
| 24 | 35.9 ± 0.2 |
| 25 | 37.0 ± 0.2 |
| 26 | 39.4 ± 0.2 |
| 27 | 42.2 ± 0.2 |
| 28 | 43.3 ± 0.2 |
| 29 | 46.8 ± 0.2 |
| 30 | 48.7 ± 0.2 |
| 31 | 50.8 ± 0.2 |
| 32 | 52.7 ± 0.2 |
| 33 | 55.2 ± 0.2 |
| 34 | 55.7 ± 0.2 |
| 35 | 57.8 ± 0.2 |

Where used by a consumer, a final serving size of the clinoptilolite fragments may be present in a concentration from about 100 mcg/ml to about 1,000 mcg/ml. In a certain embodiment, the clinoptilolite fragments may be present in a concentration of about 350 mcg/ml. In another embodiment, the clinoptilolite fragments may be present in a concentration of 750 mcg/ml. The clinoptilolite fragments may also be combined together or complexed with vitamin C, for example, in an amount from about 0.5 mg/ml to about 7.0 mg/ml. Other suitable concentrations may also be employed.

In further embodiments of the present disclosure, the aqueous solution of water-soluble hydrolyzed clinoptilolite fragments may include additional ingredients, as described hereinbelow. The additional ingredients may be used individually with the clinoptilolite fragments, alone or in combination with vitamin C as described hereinabove, or in combination with one or more of the additional ingredients detailed below. Various concentrations and combinations of the clinoptilolite fragments with Vitamin C and the additional ingredients are contemplated and considered within the scope of the present disclosure.

The additional ingredients may include resveratrol, for example. Resveratrol is also known as trans-3,4',5-Trihydroxystilbene. Resveratrol may have certain health benefits, for example, it may positively impact vascular health and heart health. In certain embodiments, the resveratrol is present in a concentration from about 20 mcg/ml to about 4,000 mcg/ml. In a most particular embodiment, the Resveratrol is present in a concentration from about 100 mcg/ml to about 2,000 mcg/ml. It should be appreciated that the hydrolyzed clinoptilolite fragments alone or the complex of hydrolyzed clinoptilolite fragments with vitamin C may increase the solubility of resveratrol and may act as a carrier for cellular delivery. One of ordinary skill in the art may select other suitable concentrations for the resveratrol, as desired.

The additional ingredient may include allicin. Allicin is also known as S-Prop-2-en-1-yl prop-2-ene-1-sulfinothioate. Allicin may have certain health benefits, for example, Allicin may desirably reduce inflammation. In certain embodiments, the allicin is present in a concentration from about 1,000 mcg/ml to about 20,000 mcg/ml. In a most particular embodiment, the allicin is present in a concentration from about 2,000 mcg/ml to about 10,000 mcg/ml. It should be appreciated that the hydrolyzed clinoptilolite fragments alone or the complex of hydrolyzed clinoptilolite fragments with vitamin C may increase the stability of allicin, which has a low melting temperature, and may act as a carrier for cellular delivery. One of ordinary skill in the art may select other suitable concentrations for the allicin, as desired.

The additional ingredient may include alpha lipoic acid (ALA). ALA is also known as (R)-5-(1,2-Dithiolan-3-yl) pentanoic acid. ALA may have certain health benefits, for example, ALA may desirably reduce oxidative stress, scavenge reactive oxygen species, and improve cellular antioxidant status. In certain embodiments, ALA is present in a concentration from about 20 mcg/ml to about 4,000 mcg/ml. In a most particular embodiment, the ALA is present in a concentration from about 200 mcg/ml to about 2,000 mcg/ml. The hydrolyzed clinoptilolite fragments alone or the complex of hydrolyzed clinoptilolite fragments with vitamin C may increase the solubility of ALA, may act as a carrier for cellular delivery, and may act as a carrier for sub-cellular delivery to mitochondria. One of ordinary skill in the art may select other suitable concentrations for the ALA, as desired.

The additional ingredient may include glutathione. Glutathione is also known as (2S)-2-Amino-4-{[(1R)-1-[(carboxymethyl)carbamoyl]-2 sulfanylethyl] carbamoyl}butanoic acid]. Glutathione may have certain health benefits, for example, glutathione may desirably reduce oxidative stress, scavenge reactive oxygen species, and improve cellular antioxidant status. In certain embodiments, glutathione is present in a concentration from about 20 mcg/ml to about 4,000 mcg/ml. In a most particular embodiment, the glutathione is present in a concentration from about 200 mcg/ml to about 2,000 mcg/ml. The hydrolyzed clinoptilolite fragments alone or the complex of hydrolyzed clinoptilolite fragments with vitamin C may increase the oral bioavailability of glutathione and may act as a carrier for cellular delivery. One of ordinary skill in the art may select other suitable concentrations for the glutathione, as desired.

The additional ingredient may include pyrroloquinoline quinone (PQQ). PQQ is also known as 4,5-dioxo-1H,4H,5H-pyrrolo[2,3-f]quinoline-2,7,9-tricarboxylic acid. PQQ may have certain health benefits, for example, PQQ may desirably reduce inflammatory status, enhance cognitive function, improve memory, improve cellular antioxidant status, provide cardiovascular support, help reverse liver damage from fatty liver disease, help reverse mitochondrial damage, help immune system. In certain embodiments, PQQ is present in a concentration from about 2 mcg/ml to about 300 mcg/ml. In a most particular embodiment, the PQQ is present in a concentration from about 10 mcg/ml to about 120 mcg/ml. The hydrolyzed clinoptilolite fragments alone or the complex of hydrolyzed clinoptilolite fragments with vitamin C may increase the oral bioavailability of PQQ and may act as a carrier for cellular delivery. One of ordinary skill in the art may select other suitable concentrations for the PQQ, as desired.

The additional ingredient may include quercetin is also known as 2-(3,4-dihydroxyphenyl)-3,5,7-trihydroxy-4H-chromen-4-one. Quercetin may have certain health benefits, for example, quercetin may reduce oxidative stress, provide cardiovascular support, help reduce inflammation. In certain embodiments, quercetin is present in a concentration from about 200 mcg/ml to about 20,000 mcg/ml. In a most particular embodiment, the quercetin is present in a concentration from about 1,000 mcg/ml to about 10,000 mcg/ml. The hydrolyzed clinoptilolite fragments alone or the complex of hydrolyzed clinoptilolite fragments with vitamin C may standardize the bioavailability of quercetin, which has a rapid clearance and short half-life. The hydrolyzed clinoptilolite fragments alone or the complex of hydrolyzed clinoptilolite fragments with vitamin C may also act as a carrier for cellular delivery. One of ordinary skill in the art may select other suitable concentrations for the quercetin, as desired.

Although described hereinabove with respect to aqueous solutions, it should be understood that the composition may be formulated in any dosage form suitable for oral administration, including one or more tablets or manufactured or artificial capsules, a manufactured or compounded liquid or slurry form, or as a manufactured powder or granulate. As non-limiting examples, suitable ingredients for the manufactured capsules can include wax, cellulose, starches, gelatin, and combinations thereof. A skilled artisan may also select other suitable dosage forms, as desired.

Advantageously, the process of the present disclosure, which creates water-soluble hydrolyzed clinoptilolite fragments from clinoptilolite, also minimizes a leaching of free heavy metals into the water solution. This is very important in use, given that free heavy metals are toxic. In contrast, "bound" (into the clinoptilolite crystal) heavy metals are not toxic. The process of the present disclosure does not release any significant amount of heavy metals from their bound state within the water solution of the water soluble hydrolyzed clinoptilolite fragments. The process of the present disclosure, results in the production of a water solution of water soluble hydrolyzed clinoptilolite fragments where the concentration of the "free heavy metals" in this solution satisfy established standards of safety.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A composition comprising: water-soluble clinoptilolite fragments and an additional ingredient selected from the group consisting of resveratrol, allicin, alpha lipoic acid, glutathione, pyrroloquinoline quinone, quercetin, and combinations thereof,
    wherein the clinoptilolite fragments and the additional ingredient are in an aqueous solution, and there is substantially no suspended clinoptilolite in the composition, and
    wherein 91-98 percent of the clinoptilolite fragments have a particle size from 0.1 microns to 1.0 microns.

2. The composition of claim 1, wherein the additional ingredient is resveratrol.

3. The composition of claim 2, wherein resveratrol is present in a concentration of about 20 mcg/ml to about 4,000 mcg/ml and the clinoptilolite fragments are present in a concentration of about 100 mcg/ml to about 1,000 mcg/ml.

4. The composition of claim 1, wherein the additional ingredient is allicin.

5. The composition of claim 4, wherein allicin is present in a concentration of about 1,000 mcg/ml to about 20,000 mcg/ml and the clinoptilolite fragments are present in a concentration of about 500 mcg/ml to about 10,000 mcg/ml.

6. The composition of claim 1, wherein the additional ingredient is alpha lipoic acid.

7. The composition of claim 6, wherein alpha lipoic acid is present in a concentration of about 20 mcg/ml to about 4,000 mcg/ml and the clinoptilolite fragments are present in a concentration of about 100 mcg/ml to about 1,000 mcg/ml.

8. The composition of claim 1, wherein the additional ingredient is glutathione.

9. The composition of claim 8, wherein glutathione is present in a concentration of about 100 mcg/ml to about 2,000 mcg/ml and the clinoptilolite fragments are present in a concentration of about 100 mcg/ml to about 1,000 mcg/ml.

10. The composition of claim 1, wherein the additional ingredient is pyrroloquinoline.

11. The composition of claim 10, wherein pyrroloquinoline is present in a concentration of about 2 mcg/ml to about 300 mcg/ml and the clinoptilolite fragments are present in a concentration of about 100 mcg/ml to about 1,000 mcg/ml.

12. The composition of claim 1, wherein the additional ingredient is quercetin.

13. The composition of claim 12, wherein quercetin is present in a concentration of about 200 mcg/ml to about 20,000 mcg/ml and the clinoptilolite fragments are present in a concentration of about 100 mcg/ml to about 1,000 mcg/ml.

14. The composition of claim 1, wherein the clinoptilolite fragments and the additional ingredient are provided in the form of a tablet or manufactured or artificial capsule, a manufactured or compounded liquid or slurry, or as a manufactured powder or granulate.

15. The composition of claim 1, wherein 1-8 percent of the clinoptilolite fragments have a particle size from 1.0 microns to 8.0 microns.

16. The composition of claim 1, wherein the water-soluble clinoptilolite fragments include fragments having molecular weights ranging from 100 Daltons to 1000 Daltons.

17. The composition of claim 1, wherein the water-soluble clinoptilolite fragments are derived from zeolite comprising about 99% clinoptilolite, the clinoptilolite comprising sodium aluminosilicate.

18. The composition of claim 1, further comprising vitamin C in a concentration of 0.5 mg/ml to 7.0 mg/ml.

* * * * *